US008939908B2

(12) United States Patent
Suzuki et al.

(10) Patent No.: US 8,939,908 B2
(45) Date of Patent: Jan. 27, 2015

(54) ULTRASONIC BLOOD VESSEL INSPECTING APPARATUS

(75) Inventors: Hidenori Suzuki, Nagoya (JP); Katsushi Iikubo, Nagoya (JP); Chikao Harada, Nagoya (JP); Hiroshi Masuda, Nagoya (JP)

(73) Assignee: Unex Corporation, Aichi (JP)

( * ) Notice: Subject to any disclaimer, the term of this patent is extended or adjusted under 35 U.S.C. 154(b) by 478 days.

(21) Appl. No.: 13/383,866

(22) PCT Filed: Jul. 16, 2009

(86) PCT No.: PCT/JP2009/062909
§ 371 (c)(1),
(2), (4) Date: Jan. 13, 2012

(87) PCT Pub. No.: WO2011/007439
PCT Pub. Date: Jan. 20, 2011

(65) Prior Publication Data
US 2012/0116227 A1    May 10, 2012

(51) Int. Cl.
*A61B 6/00*    (2006.01)
*A61B 8/08*    (2006.01)
*A61B 5/02*    (2006.01)
*A61B 8/00*    (2006.01)

(52) U.S. Cl.
CPC .......... *A61B 8/0858* (2013.01); *A61B 5/02007* (2013.01); *A61B 8/461* (2013.01)
USPC .......... 600/437; 600/407; 600/443; 600/444; 600/445; 600/446; 600/447; 600/454; 600/459

(58) Field of Classification Search
USPC .................. 600/407, 437, 443–447, 454, 459
See application file for complete search history.

(56) References Cited

U.S. PATENT DOCUMENTS

| 6,132,373 | A  | * | 10/2000 | Ito et al. | 600/437 |
| 6,817,982 | B2 | * | 11/2004 | Fritz et al. | 600/443 |
| 6,835,177 | B2 | * | 12/2004 | Fritz et al. | 600/443 |
| 7,727,153 | B2 | * | 6/2010  | Fritz et al. | 600/449 |

(Continued)

FOREIGN PATENT DOCUMENTS

| CN | 101431942 A | 5/2009 |
| JP | A-2007-0222291 | 9/2007 |

(Continued)

OTHER PUBLICATIONS

Suzuki et al., Machine Translation of Japanese Application No. 2007-263805, Published on Apr. 30, 2009. Having corresponding US Patent Pub. No. 2010/0210946. pp. 1-63.*

(Continued)

*Primary Examiner* — James Kish
(74) *Attorney, Agent, or Firm* — Oliff PLC

(57) ABSTRACT

An ultrasonic blood vessel inspecting apparatus provided with a longitudinal cross sectional blood vessel image generating portion configured to generate a longitudinal cross sectional image of a blood vessel located below a skin of a live body, on the basis of reflected wave signals of an ultrasonic wave by using an ultrasonic probe placed on the skin of said live body, includes: an index value calculating portion configured to calculate an index value indicative of a degree of clarity of an image which represents an intima-media complex of said blood vessel and which exists within said longitudinal cross sectional image of the blood vessel.

7 Claims, 16 Drawing Sheets

(56) References Cited

U.S. PATENT DOCUMENTS

| | | | |
|---|---|---|---|
| 2003/0199762 A1* | 10/2003 | Fritz et al. | 600/437 |
| 2004/0116808 A1* | 6/2004 | Fritz et al. | 600/437 |
| 2005/0119555 A1* | 6/2005 | Fritz et al. | 600/410 |
| 2006/0184034 A1* | 8/2006 | Haim et al. | 600/459 |
| 2007/0032725 A1 | 2/2007 | Watanabe et al. | |
| 2007/0038084 A1* | 2/2007 | Burla et al. | 600/437 |
| 2009/0163811 A1 | 6/2009 | Fukumoto et al. | |
| 2010/0210946 A1* | 8/2010 | Harada et al. | 600/443 |
| 2011/0105902 A1* | 5/2011 | Kume et al. | 600/443 |

FOREIGN PATENT DOCUMENTS

| | | |
|---|---|---|
| JP | A-2009-089911 | 4/2009 |
| JP | A-2009-0153573 | 7/2009 |
| WO | WO 2005/020821 A1 | 3/2005 |

OTHER PUBLICATIONS

International Search Report issued in International Application No. PCT/JP2009/062909 dated Aug. 25, 2009 (with translation).

Jul. 23, 2013 Office Action issued in Japanese Patent Application No. 2011-522663 (with English translation).

* cited by examiner

ULTRASONIC BLOOD VESSEL INSPECTING APPARATUS

TECHNICAL FIELD

The present invention relates to techniques for generating a cross sectional image of a blood vessel by using an ultrasonic probe.

BACKGROUND ART

An ultrasonic detector array having a plurality of ultrasonic oscillators which are linearly arranged is used to measure a diameter of a blood vessel (such as an arterial vessel) located below a skin of a live body. Patent Document 1 discloses an example of an ultrasonic blood vessel inspecting apparatus configured to measure a lumen diameter and a thickness of an intima-media complex of the above-described blood vessel, by using an ultrasonic probe of an H-type which consists of mutually parallel first and second ultrasonic detector arrays and a third ultrasonic detector array connecting intermediate portions of the first and second ultrasonic detector arrays, and which is positioned such that the third ultrasonic detector array is parallel to the blood vessel and aligned with a centerline of the blood vessel. The ultrasonic blood vessel inspecting apparatus disclosed in this Patent Document 1 is provided with a multi-axes drive device which is operated to position the above-described ultrasonic probe on the basis of a first short-axis ultrasonic image obtained by the above-described first ultrasonic detector array and a second short-axis ultrasonic image obtained by the above-described second ultrasonic detector array, such that a distance between the above-described first ultrasonic detector array and the centerline of the above-described blood vessel and a distance between the above-described second ultrasonic detector array and the centerline of the blood vessel are equal to each other. Further, the above-described multi-axes drive device is operated to position the above-described ultrasonic probe such that an image of the above-described blood vessel is positioned in a widthwise central portion of each of the above-described first and second short-axis ultrasonic images.

PRIOR ART DOCUMENT

Patent Document

Patent Document 1: JP-2009-089911 A

SUMMARY OF THE INVENTION

Object Achieved By the Invention

Actually, however, the blood vessel right below the above-described third ultrasonic detector array may be curved, so that mere automatic positioning of the ultrasonic probe in the ultrasonic blood vessel inspecting apparatus of the above-identified Patent Document 1 does not necessarily enable the above-described third ultrasonic detector array to obtain a long-axis ultrasonic image which is clear enough to permit measurement of the diameter of the blood vessel. Therefore, a fine positional adjustment of the ultrasonic probe is made by a manual operation by the operator after the automatic positioning of the ultrasonic probe, for example, to obtain the long-axis ultrasonic image which is clear enough to permit the measurement of the blood vessel diameter. This manual positioning (fine positional adjustment) of the ultrasonic probe by the operator requires a high manipulation skill, resulting in a problem of reduced manual positioning efficiency.

The present invention was, made in view of the background art described above. It is accordingly an object of this invention to provide an ultrasonic blood vessel inspecting apparatus which is capable of obtaining a clear ultrasonic image of a blood vessel with high efficiency, even where the operator's manipulation skill is low.

Means for Achieving the Object

The object indicated above is achieved according to the principle of this invention, which provides an ultrasonic blood vessel inspecting apparatus (a) provided with longitudinal cross sectional blood vessel image generating means for generating a longitudinal cross sectional image of a blood vessel located below a skin of a live body, on the basis of reflected wave signals of an ultrasonic wave by using an ultrasonic probe placed on the skin of the above-described live body, (b) characterized by comprising index value calculating means for calculating an index value indicative of a degree of clarity of an image which represents an intima-media complex of the above-described blood vessel and which exists within the above-described longitudinal cross sectional image of the blood vessel.

Advantages of the Invention

According to the present invention described above, the operator of the ultrasonic blood vessel inspecting apparatus is not required to determine the degree of clarity of the image directly from the longitudinal cross sectional image of the above-described blood vessel (longitudinal cross sectional blood vessel image), but can objectively determine the degree of clarity of the image from the index value indicative of the degree of clarity of the image representing the intima-media complex of the above-described blood vessel, so that the operator can easily make a fine positional adjustment of the ultrasonic probe so as to improve the index values, whereby the longitudinal cross sectional blood vessel image can be efficiently obtained with a high degree of clarity, even where the operator's manipulation skill is low.

Preferably, the above-described index value calculating means calculates a front wall portion image clarity index value indicative of the degree of clarity of an image of a front wall portion of the above-described intima-media complex within the above-described longitudinal cross sectional image of the blood vessel, and a back wall portion image clarity index value indicative of the degree of clarity of an image of a back wall portion of the above-described intima-media complex within the above-described longitudinal cross sectional image of the blood vessel, the above-described front wall portion being one of opposite wall portions of the blood vessel on the side of the above-described ultrasonic probe while the above-described back wall portion being the other of the opposite wall portions which is remote from the above-described ultrasonic probe. In this case, the above-described ultrasonic probe can be positioned to increase the degree of clarity of the images of the above-described front wall portion and back wall portion within the longitudinal cross sectional image of the blood vessel.

Also preferably, (a) the ultrasonic blood vessel inspecting apparatus further comprises reflected wave recognition control means configured to implement a reflected wave recognition control for each of a plurality of the above-described reflected wave signals received by the above-described ultrasonic probe at mutually different positions of reception in a longitudinal direction of the above-described blood vessel, and for each of the above-described front wall portion and the above-described back wall portion, to detect according to a relationship between a magnitude of each reflected wave signal and a position in a diametric direction of the above-described blood vessel: a first peak of each reflected wave signal at which the magnitude is larger than a predetermined first peak determining threshold value; a bottom of each reflected wave signal which is generated at a position of the above-described blood vessel located outwardly of the position of generation of the above-described first peak in the diametric direction of the above-described blood vessel and at which the magnitude is smaller than a predetermined bottom determining threshold value; and a second peak of each reflected wave signal which is generated at a position of the above-described blood vessel located outwardly of the position of generation of the above-described first peak in the diametric direction of the above-described blood vessel but located within a spacing distance from the position of generation of the first peak less than a predetermined peak-to-peak distance threshold value, with the above-described bottom being located therebetween, and at which the magnitude is larger than a predetermined second peak determining threshold value, (b) and the above-described index value calculating means calculates the above-described front wall portion image clarity index value on the basis of a number of the reflected wave signals all of the above-described first peak, the above-described bottom and the above-described second peak of which have been detected by the above-described reflected wave recognition control implemented by the above-described reflected wave recognition control means for the above-described front wall portion, and the above-described back wall portion image clarity index value on the basis of a number of the reflected wave signals all of the above-described first peak, the above-described bottom and the above-described second peak of which have been detected by the above-described reflected wave recognition control implemented by the above-described reflected wave recognition control means for the above-described back wall portion. In this case, the above-described front wall portion image clarity index value and the above-described back wall portion image clarity index value are calculated on the basis of non-fluctuating parameters, so that the above-described front wall portion image clarity index values and the above-described back wall portion image clarity index values which are calculated upon different blood vessel inspections can be compared with each other.

Also preferably, the above-described reflected wave recognition control means implements the above-described reflected wave recognition control for those of the above-described reflected wave signals which are received within a predetermined observation range in the longitudinal direction of the above-described blood vessel. In this case, it is possible to reduce a control load in the calculation of the above-described front wall portion image clarity index value and the above-described back wall portion image clarity index value, as compared where the above-described reflected wave recognition control is implemented for all of the plurality of the above-described reflected wave signals received by the above-described ultrasonic probe to generate the above-described longitudinal cross sectional blood vessel image.

Also preferably, the magnitude of each reflected wave signal is an amplitude of each reflected wave signal, or a brightness value obtained by conversion of the amplitude of each reflected wave signal, which brightness value is used to display the longitudinal cross sectional image of the above-described blood vessel. In this case, the above-described first peak, the above-described bottom and the above-described second peak can be easily detected.

Also preferably, (a) the above-described ultrasonic probe is provided with a pair of parallel ultrasonic detector arrays consisting of a first short-axis ultrasonic detector array and a second short-axis ultrasonic detector array each of which has a plurality of ultrasonic oscillators arranged linearly in a direction perpendicular to a longitudinal direction of the above-described blood vessel, and a long-axis ultrasonic detector array which is disposed adjacent to an intermediate portion of one or both of the first short-axis ultrasonic detector array and the second short-axis ultrasonic detector array and which has a plurality of ultrasonic oscillators arranged lineayly in the longitudinal direction of the above-described blood vessel, the above-described first and second short-axis ultrasonic detector arrays and the above-described long-axis ultrasonic detector array lying in one plane, and (b) the above-described longitudinal cross sectional blood vessel image generating means generates the longitudinal cross sectional image of the above-described blood vessel, on the basis of the reflected wave signals of the above-described ultrasonic wave received by the above-described long-axis ultrasonic detector array. In this case, the above-described longitudinal cross sectional blood vessel image can be generated by using the ultrasonic wave probe which is practically available.

Also preferably, the ultrasonic blood vessel inspecting apparatus further comprises (a) an image display device having a first short-axis image display region for displaying an ultrasonic image obtained by the above-described first short-axis ultrasonic detector array, a second short-axis image display region for displaying an ultrasonic image obtained by the above-described second short-axis ultrasonic detector array, and a long-axis image display region for displaying the longitudinal cross sectional blood vessel image of the above-described blood vessel, (b) a multi-axes drive device configured to position the above-described ultrasonic probe, (c) short-axis image position establishing means for operating the above-described multi-axes drive device to position the above-described ultrasonic probe such that a distance between the above-described first short-axis ultrasonic detector array and a center of the above-described blood vessel is equal to a distance between the above-described second short-axis ultrasonic detector array and the center of the above-described blood vessel, and such that the image of the above-described blood vessel is located at a widthwise central portion of each of the above-described first short-axis image display region and the above-described second short-axis image display region, and (d) ultrasonic probe position rectifying means for operating the above-described multi-axes drive device to position the above-described ultrasonic probe after completion of positioning of the above-described ultrasonic probe under the control of the above-described short-axis image position establishing means, such that a value calculated on the basis of the above-described front wall portion image clarity index value and the above-described back wall portion image clarity index value is held within a predetermined target range. In this case, an operator's load of manipulation can be reduced. Further, the longitudinal cross sectional blood vessel image can be made clearer even where the operator's manipulation skill is considerably low.

Also preferably, the ultrasonic blood vessel inspecting apparatus further comprises (a) blood vessel diameter measuring means for measuring in advance a rest-time diameter of the above-described blood vessel before releasing of the above-described blood vessel from blood flow obstruction, and a maximum diameter of the above-described blood vessel after the releasing of the above-described blood vessel from the blood flow obstruction, and calculating a maximum value of a diameter change ratio of the above-described blood vessel after the releasing of the above-described blood vessel from the blood flow obstruction, with respect to the rest-time diameter of the above-described blood vessel, and (b) and the above-described index value calculating means calculates an index value indicative of a degree of reliability of the maximum value of the diameter change ratio of the above-described blood vessel calculated by the above-described blood vessel diameter measuring means after the releasing of the above-described blood vessel with respect to the rest-time diameter of the above-described blood vessel, on the basis of the above-described front wall portion image clarity index value and the above-described back wall portion image clarity index value upon measurement of the above-described rest-time diameter, and the above-described front wall portion image clarity index value and the above-described back wall portion image clarity index value upon measurement of the above-described maximum diameter. Where a plurality of maximum values of the diameter change ratio after the blood vessel releasing from the blood flow obstruction with respect to the rest-time diameter of the above-described blood vessel are measured and compared with each other, the above-described index value indicative of the degree of reliability of each maximum value can be used to eliminate those of the plurality of maximum values the accuracy of measurement of which is low, so that the reliability of a result of FMD evaluation, for instance, can be further improved.

Also preferably, the above-described index value calculating means commands an image display device to display the above-described front wall portion image clarity index value and the above-described back wall portion image clarity index value, as respective images which are continuously variable according to the above-described index values and which are comparable with each other. In this case, the operator can intuitively perceive the degrees of clarity of the images of the above-described front wall portion and the above-described back wall portion, and more efficiently improve the clarity of the images, than where the degrees of clarity of the images are indicated by numerical values.

MODE FOR CARRYING OUT THE INVENTION

Embodiments of the present invention will be described in detail by reference to the drawings.

Embodiment 1

Figure 1:
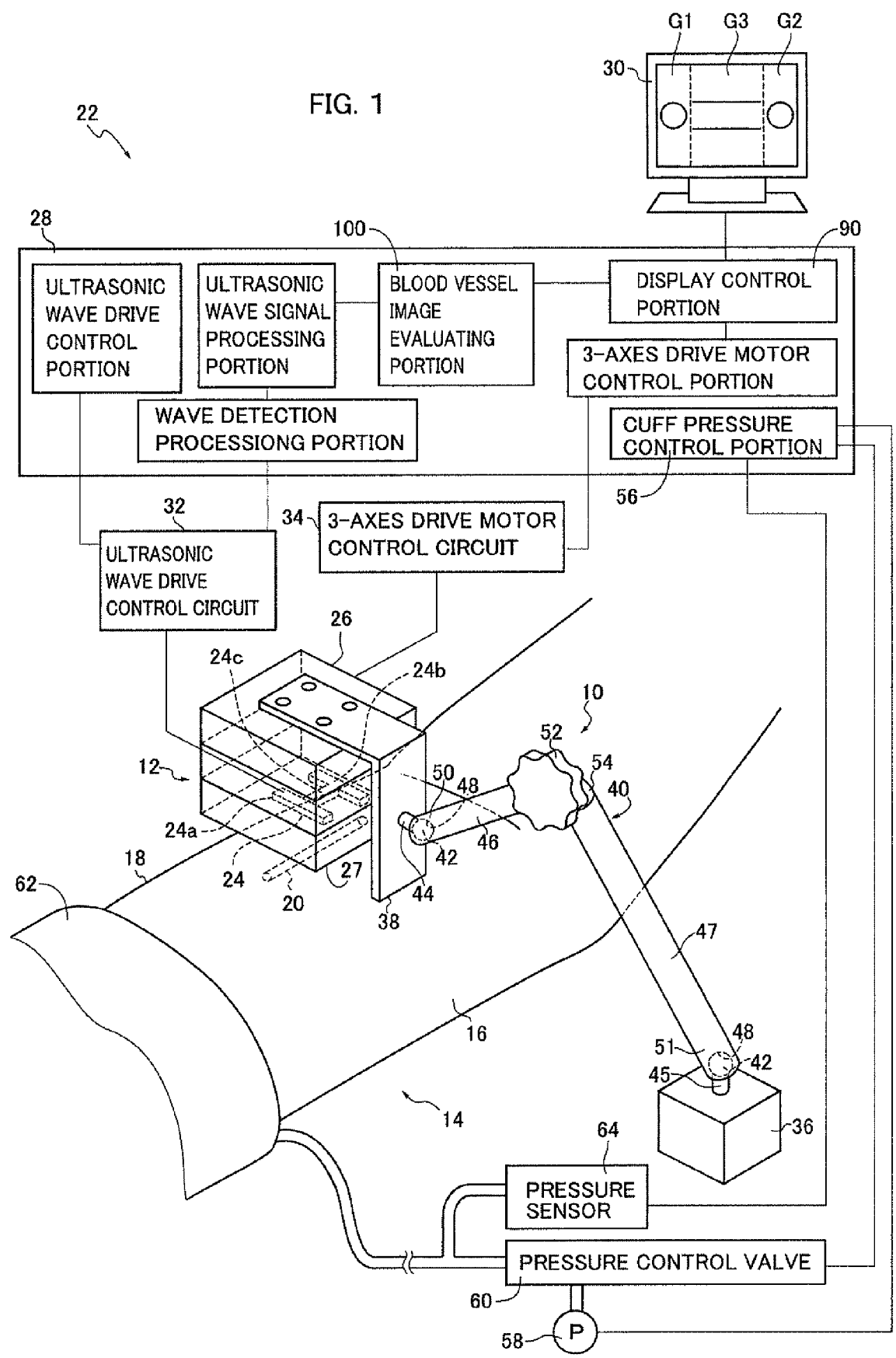
FIG. 1 is a view showing an overall arrangement of an ultrasonic blood vessel inspecting apparatus according to one embodiment of this invention.

FIG. 1 is the view showing an overall arrangement of an ultrasonic blood vessel inspecting apparatus 22 (hereinafter referred to as "blood vessel inspecting apparatus 22") constructed to perform non-invasion ultrasonic diagnosis of a blood vessel 20 such as an arterial vessel immediately below a skin 18 (more strictly, an outer epidermis) of a brachium 16 of a live body 14, through the skin 18, using a probe unit 12 held by a sensor holder 10.

The probe unit 12, which functions as a sensor for detecting vital body information relating to the blood vessel 20, that is, blood vessel parameters, is provided with an H-type ultrasonic probe 24, and a multi-axes drive device (positioning device) 26 for linearly positioning the ultrasonic probe 24 in x, y and z directions and angularly positioning the ultrasonic probe 24 about x and z axes. The ultrasonic probe 24 has a pair of mutually parallel ultrasonic detector arrays consisting of a first short-axis ultrasonic detector array 24a and a second short-axis ultrasonic detector array 24b, and a long-axis ultrasonic detector array 24c which connects the first and second short-axis ultrasonic arrays 24a and 24b at longitudinally intermediate portions thereof. The ultrasonic detector arrays 24a, 24b and 24c lie on one plane, namely, on a flat detection plane 27. Each of the first short-axis ultrasonic detector array 24a, second short-axis ultrasonic detector array 24b, and long-axis ultrasonic detector array 24c is an elongate member having a multiplicity of ultrasonic oscillators (vibrators) $a_1$-$a_n$ which are formed of a piezoelectric ceramic material and which are arranged linearly.

Figure 2:
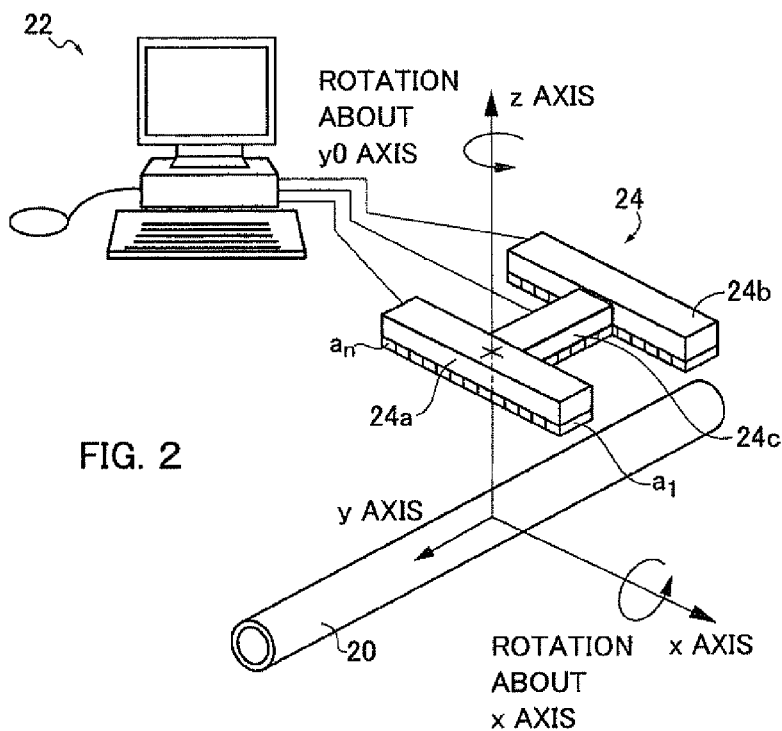
FIG. 2 is a view for explaining x, y and z axes of a rectangular coordinate system for indicating an attitude of an ultrasonic probe used by the ultrasonic blood vessel inspecting apparatus of FIG. 1, with respect to the blood vessel.

FIG. 2 is the view for explaining the x, y and z axes of a rectangular coordinate system used in the present embodiment. The x axis is parallel to the longitudinal direction of the first short-axis ultrasonic detector array 24a, and located right below the first short-axis ultrasonic detector array 24a, and passes a vertical position of the blood vessel 20 or a point vertically close to that vertical position. The y axis is parallel to the longitudinal direction of the long-axis ultrasonic detector array 24c, and is perpendicular to the x axis, while the z axis passes a point of intersection between the longitudinal direction of the first short-axis ultrasonic detector array 24a and the longitudinal direction of the long-axis ultrasonic detector array 24c, and is perpendicular o the above-described x and y axes. The ultrasonic probe 24 is translated along the x axis and rotated about the x and z axes by the multi-axes drive device 26.

Figure 3:
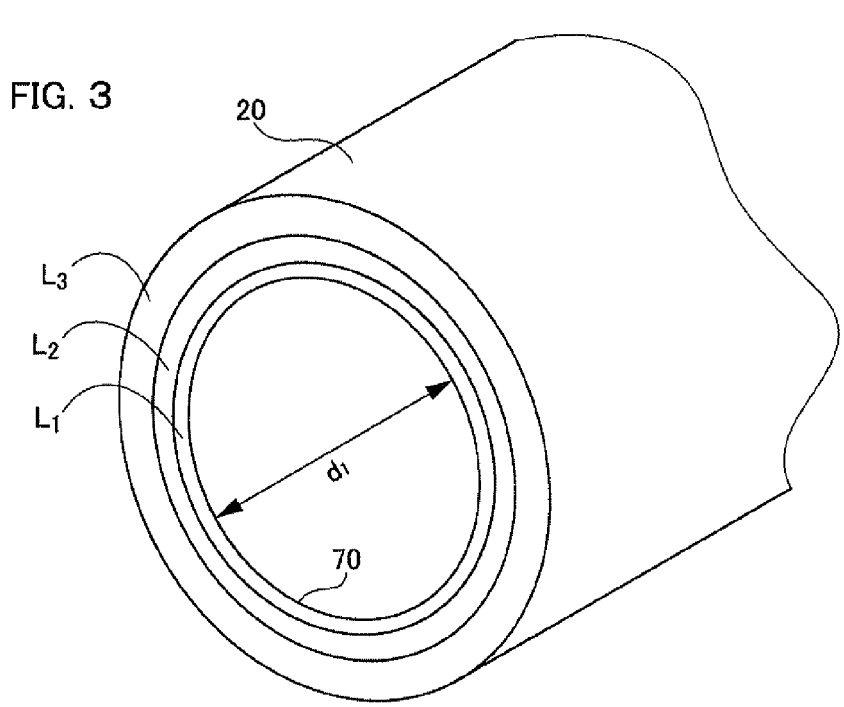
FIG. 3 is an enlarged view for explaining a multi-layered structure of a blood vessel which is a subject irradiated with an ultrasonic wave generated by the ultrasonic probe of FIG. 2.

As shown in FIG. 3, the blood vessel 20 which is an arterial vessel of the brachium, for instance, has a three-layered structure consisting of an inner layer $L_1$, an intermediate layer $L_2$ and an outer layer $L_3$. Since the reflection of an ultrasonic wave takes place in boundary portions having different values of acoustic impedance, a boundary surface between the blood in the lumen of the blood vessel and the inner layer $L_1$, and a boundary surface between the intermediate layer $L_2$ and the outer layer $L_3$ are displayed as white regions, and the tissue is displayed by white and black spots.

Referring back to FIG. 1, the blood vessel inspecting apparatus 22 is provided with an electronic control device 28, a monitoring image display device (image display device) 30, an ultrasonic wave drive control circuit 32, and a 3-axes drive motor control circuit 34. The electronic control device 28 is constituted by a so-called microcomputer having a CPU operable to process input signals according to programs preliminarily stored in a ROM, while utilizing a temporary data storage function of a RAM. The above-described electronic control device 28 is configured to command the ultrasonic wave drive control circuit 32 to apply drive signals to the first short-axis ultrasonic detector array 24a, second short-axis ultrasonic detector array 24b and long-axis ultrasonic detector array 24c of the ultrasonic probe 24 of the probe unit 12, for successively irradiating ultrasonic waves in the form of a beam in a beam forming fashion well known in the art. The irradiated ultrasonic waves are reflected as reflected ultrasonic signals, which are detected by the first and second short-axis ultrasonic detector arrays 24a, 24b and long-axis ultrasonic detector array 24c. The reflected ultrasonic signals are processed to generate ultrasonic images of a tissue under the skin 18, and the ultrasonic images are displayed on the monitoring image display device 30.

Figure 4:
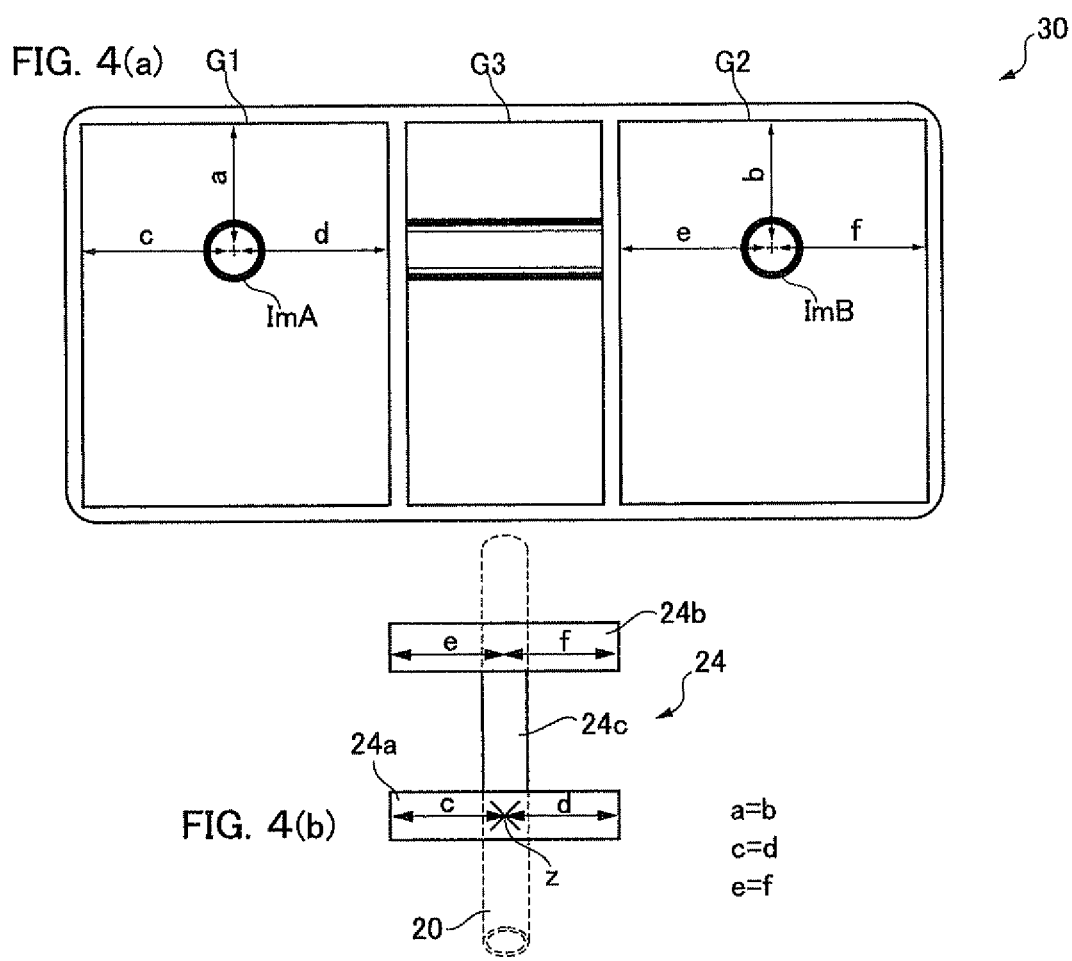
FIG. 4 is a view indicating a relative position between the ultrasonic probe positioned at a predetermined position and the blood vessel upon generation of an ultrasonic image of the blood vessel, and a monitoring image display device which displays the ultrasonic image of the blood vessel.

As indicated at (a) in FIG. 4, the monitoring image display device 30 has a first short-axis image display region G1 for displaying the ultrasonic image obtained by the first short-axis ultrasonic detector array 24a, a second short-axis image display region G2 for displaying the ultrasonic image obtained by the second short-axis ultrasonic detector array 24b, and a long-axis image display region G3 for displaying the ultrasonic image (longitudinal cross sectional blood vessel image) obtained by the long-axis ultrasonic detector array 24c. These short-axis and long-axis image display regions G1, G2 and G3 have a common vertical axis along which a depth dimension from the skin 18 is indicated. "ImA" and "ImB" indicated at (a) in FIG. 4 represent transverse cross sectional images of the blood vessel 20.

The monitoring image display device 30 is further configured to chronologically display a change ratio of the diameter of the inner layer, that is, a dilatation ratio R of the lumen diameter, for the FMD (Flow Mediated vasoDilation) evaluation.

Upon the above-described FMD evaluation and generation of the ultrasonic images of the blood vessel 20, the ultrasonic probe 24 is located at a predetermined measuring position PT1 with respect to the blood vessel 20, by the multi-axes drive device 26 which is operated according to the drive signals received from the 3-axes drive motor control circuit 34 under the control of the electronic control device 28. At the predetermined measuring position PT1, the first short-axis ultrasonic detector array 24a and the second short-axis ultrasonic detector array 24b are perpendicular to the blood vessel 20, while the long-axis ultrasonic detector array 24c is parallel to the blood vessel 20. Explained by reference to (a) and (b) in FIG. 4, the predetermined measuring position PT1 is the position at which a=b, c=d, and e=f. Namely, at this measuring position PT1, a distance between the above-described first short-axis ultrasonic detector array 24a and a center of the blood vessel 20 is equal to a distance between the above-described second short-axis ultrasonic detector array 24b and the center of the blood vessel 20, and the images of the blood vessel 20 are displayed in widthwise central positions in the first and second short-axis image display regions G1 and G2.

The sensor holder 10 is constructed to hold the probe unit 12 so as to have a predetermined attitude at the predetermined (i.e. desired) position PT1 in a three-dimensional space, such that the probe unit 12 is held in contact with the skin 18 of the brachium 16 of the live body 14, with a low pressure so as not to cause deformation of the blood vessel 20 immediately below the skin 18. Between the contact surface of the ultrasonic probe 24 of the probe unit 12 and the skin 18, there is usually interposed a well known coupling agent such as jelly, olive oil and glycerin, or a resin bag charged with water, to reduce attenuation of the ultrasonic wave, and reflection and scattering of the ultrasonic wave at the boundary surfaces, for thereby obtaining clear ultrasonic images.

The above-described sensor holder 10 is provided with a magnet stand 36, unit fixture 38, connecting members 44, 45, and a universal arm 40. The magnet stand 36 is fixed with a magnetic attraction force, for example, to a desk or a pedestal, and the above-described probe unit 12 is fixed to the unit fixture 38. The connecting members 44, 45 are fixed at one end thereof to the unit fixture 38 and the magnet stand 36, respectively, and have spherical distal end portions 42. The universal arm 40 connects the magnet stand 36 and the unit fixture 38 to each other via the connecting members 44, 45 and supports the magnet stand 36 and unit fixture 38, such that the magnet stand 36 and the unit fixture 38 are movable relative to each other. The universal arm 40 has two links 46, 47 pivotably connected to each other, universal joint portions 50, 51 having respective engaging holes 48, and a pivotal joint portion 54. The engaging hole 48 is formed in one end portion of each of the two links 46, 47, and the above-described spherical distal end portion 42 is universally fitted in the engaging hole 48, with a predetermined force of resistance to universal motions of the links 46, 47 relative to the spherical distal end portion 42. The two links 46, 47 are pivotably connected to each other at the other end portions by the pivotal joint portion 54, which has a fixing knob 52 provided with an externally threaded portion screwed in tapped holes formed through the above-indicated other end portions of the links 46, 47, so that pivotal motions of the two links 46, 47 are prevented when the faxing knob 52 is tightened.

The multi-axes drive device 26 consists of an x-axis rotating (yawing) mechanism fixed to the unit fixture 38 and having an x-axis rotating actuator to rotate the ultrasonic probe 24 about the x axis, an x-axis translating mechanism having an x-axis translating actuator to translate the ultrasonic probe 24 along the x axis, and a z-axis rotating mechanism having a z-axis rotating actuator to rotate the ultrasonic probe 24 about the z axis. The multi-axes drive device which has the above-described structure controls the position and attitude of the ultrasonic probe 24.

The ultrasonic wave drive control circuit 32 shown in FIG. 1 is commanded by the electronic control device 28 to drive the multiplicity of linearly arranged ultrasonic oscillators (vibrators) $a_1$-$a_n$ of the above-described first short-axis ultrasonic detector array 24a, for example, such that a group of a predetermined number of the ultrasonic oscillators, for example, a group of the 15 ultrasonic oscillators $a_1$-$a_{15}$ are concurrently driven at a frequency of about 10 MHz, with a predetermined phase difference, to implement a beam forming operation to successively irradiate ultrasonic wave beams toward the blood vessel 20, such that the ultrasonic wave beams converge in the direction of arrangement of the ultrasonic oscillators. The ultrasonic wave beams are irradiated with the members of the group of the predetermined number of the ultrasonic oscillators being shifted by one oscillator per each beam forming operation, and the thus irradiated ultrasonic wave beams are scanned to detect reflected waves, which are input to the electronic control device 28.

The electronic control device 28 synthesizes an image on the basis of the above-described reflected waves, that is, a transverse cross sectional image (short-axis image) or a longitudinal cross sectional image (long-axis image) of the blood vessel 20 below the skin 18, and displays the image on the monitoring image display device (image display device) 30. Further, the electronic control device 28 calculates the diameter of the blood vessel 20, or an endothelial skin diameter (blood vessel lumen diameter) $d_1$, which is a diameter of an endothelial skin 70, on the basis of the image. In addition, the electronic control device 28 calculates the dilatation ratio (change ratio) R (%) [=100×($d_1$−$d_a$)/$d_a$] of the blood vessel lumen representative of the FMD (Flow Mediated vasoDilation reaction of the blood vessel) after ischemic reaction congestion, for evaluating the function of the endothelial skin 70 of the blood vessel. "$d_a$" in the above-indicated equation is the diameter of the blood vessel lumen at rest (base diameter or rest-time diameter).

Figure 5:
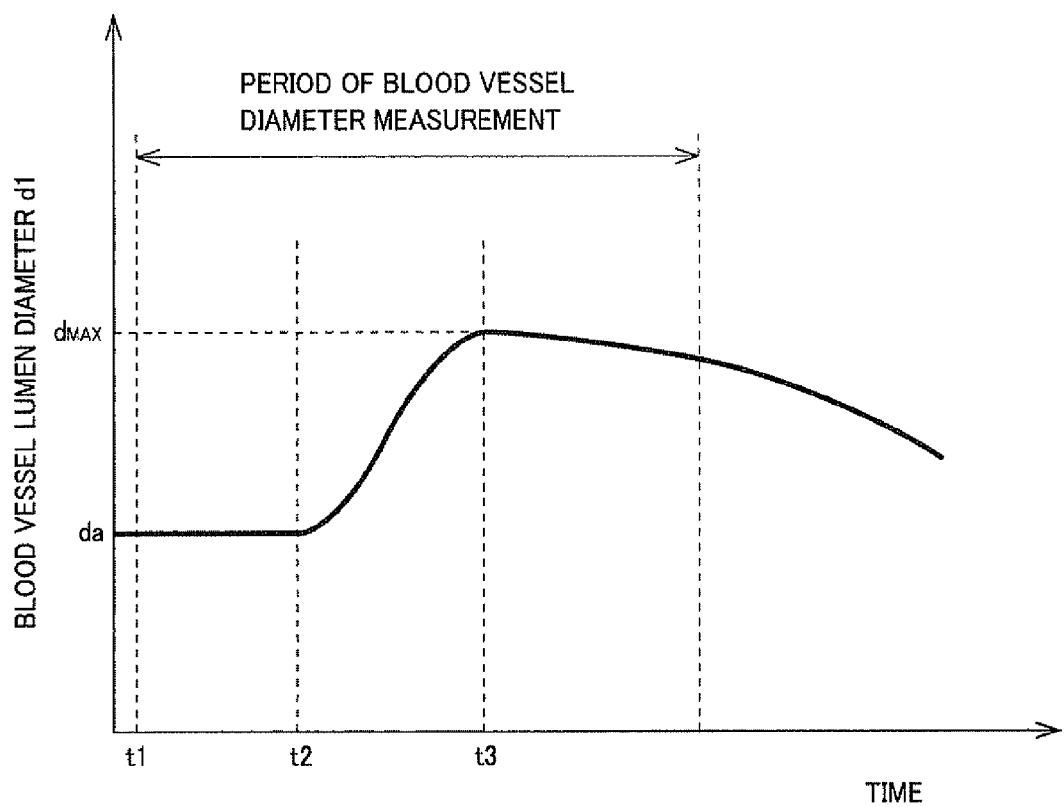
FIG. 5 is a time chart indicating an example of a change of a lumen diameter of the blood vessel after releasing of the blood vessel from blood flow obstruction, which is measured with the ultrasonic wave generated from the ultrasonic probe of FIG. 2.

FIG. 5 is the time chart indicating an example of a change of the blood vessel lumen diameter $d_1$ after releasing of the blood vessel from blood flow obstruction (bloodlessness). In the example of FIG. 5, the blood vessel is released from blood flow obstruction, at a point of time t1, and the blood vessel lumen diameter $d_1$ begins to increase at a point of time t2, and reaches a maximum value $d_{MAX}$ at a point of time t3. Thus, the dilatation ratio R of the blood vessel lumen diameter calculated by the electronic control device 28 is maximized at the point of time t3.

The above-described blood flow obstruction for the FMD evaluation is conducted by a cuff 62 which is wound on the brachium 16, as shown in FIG. 1, and an air pressure of which is controlled by a pressure control valve 60 under the control of a cuff pressure control portion 56 (cuff pressure control means 56) of the electronic control device 28. The pressure control valve 60 controls the pressure of pressurized air delivered from a pneumatic pump 58, so that the air pressure of the cuff 62 is raised to a predetermined blood flow obstruction value higher than the systolic blood pressure of the live body 14. The above-described cuff pressure control portion 56 detects the air pressure of the cuff 62 on the basis of an output signal of a pressure sensor 64 provided to detect the air pressure. In the example of FIG. 5, the air pressure of the cuff 62 is kept at the above-described blood flow obstruction value under the control of the cuff pressure control portion 56, for a predetermined length of time before a moment of releasing of the blood vessel from the blood flow obstruction, that is, before the point of time t1, and is immediately lowered to the atmospheric pressure value at the point of time t1.

Figure 6:
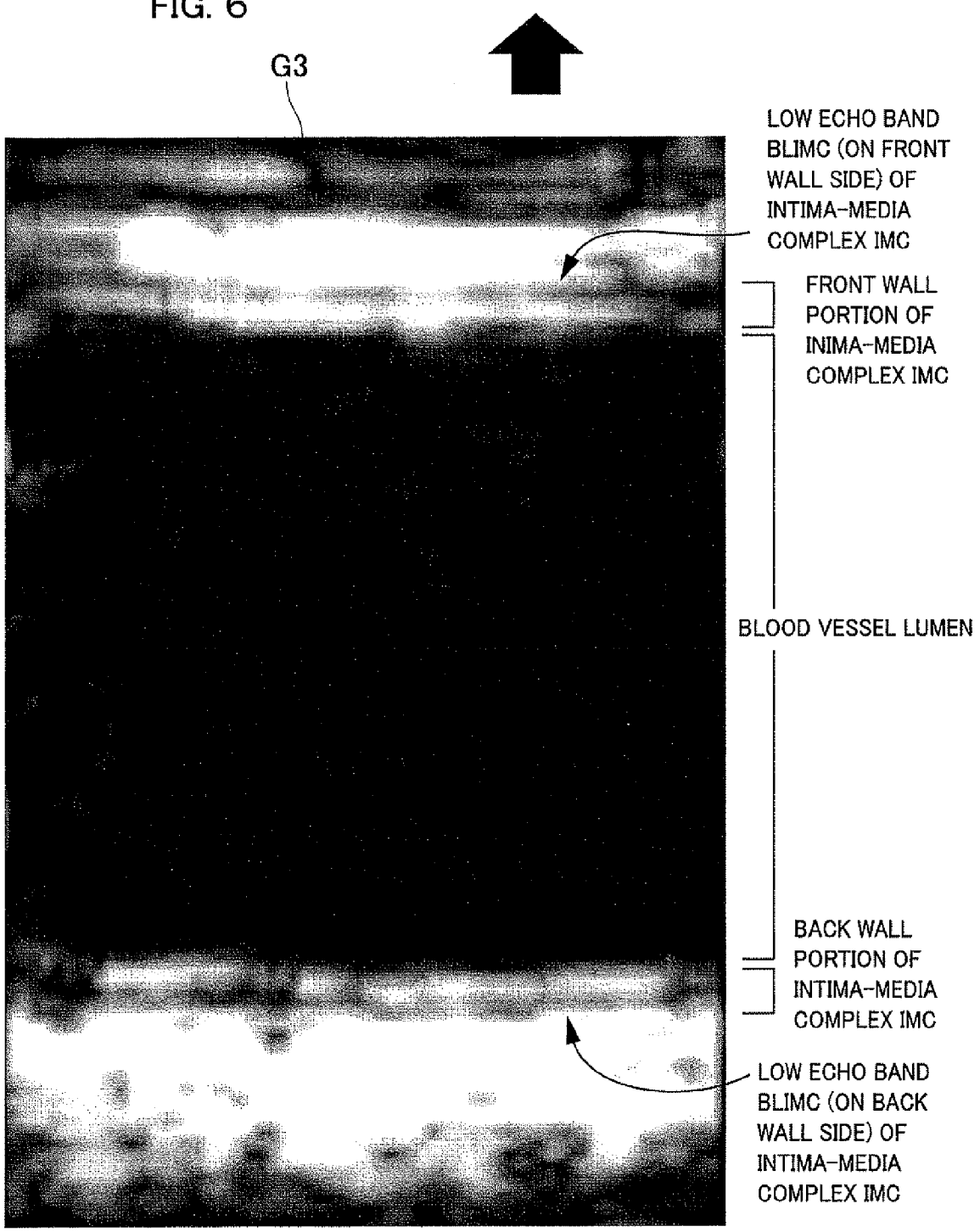
FIG. 6 is a view indicating an example of a longitudinal cross sectional image of the blood vessel displayed in a long-axis image display region of the monitoring display device of FIG. 1, where the clarity of an intima-media complex of the blood vessel wall is relatively high.

In the present embodiment wherein the ultrasonic probe 24 is located at the above-described predetermined measuring position PT1 by an operation of the multi-axes drive device 26, a longitudinal cross sectional image of the blood vessel 20 is displayed in the long-axis image displaying region G3, basically with a high degree of clarity of an intima-media complex IMC consisting of the inner layer $L_1$ and the intermediate layer L2, as shown in FIG. 6. In the longitudinal cross sectional image of the blood vessel 20 shown in FIG. 6, a low echo band $BL_{IMC}$ (black lines seen in FIG. 6) of the intima-media complex IMC is clearly displayed continuously in the longitudinal direction of the blood vessel 20, for both of a front wall portion $BR_F$ of the blood vessel 20 in cross section on the side of the ultrasonic probe 24 and a back wall portion $BR_B$ of the blood vessel 20 in cross section on the side remote from the ultrasonic probe 24. Thus, the longitudinal cross sectional image of FIG. 6 is considered to have a high degree of clarity of the image of the intima-media complex IMC. A blood vessel image diagnosis such as FMD evaluation based on this clear image can be made with a sufficiently high degree of accuracy.

Figure 7:
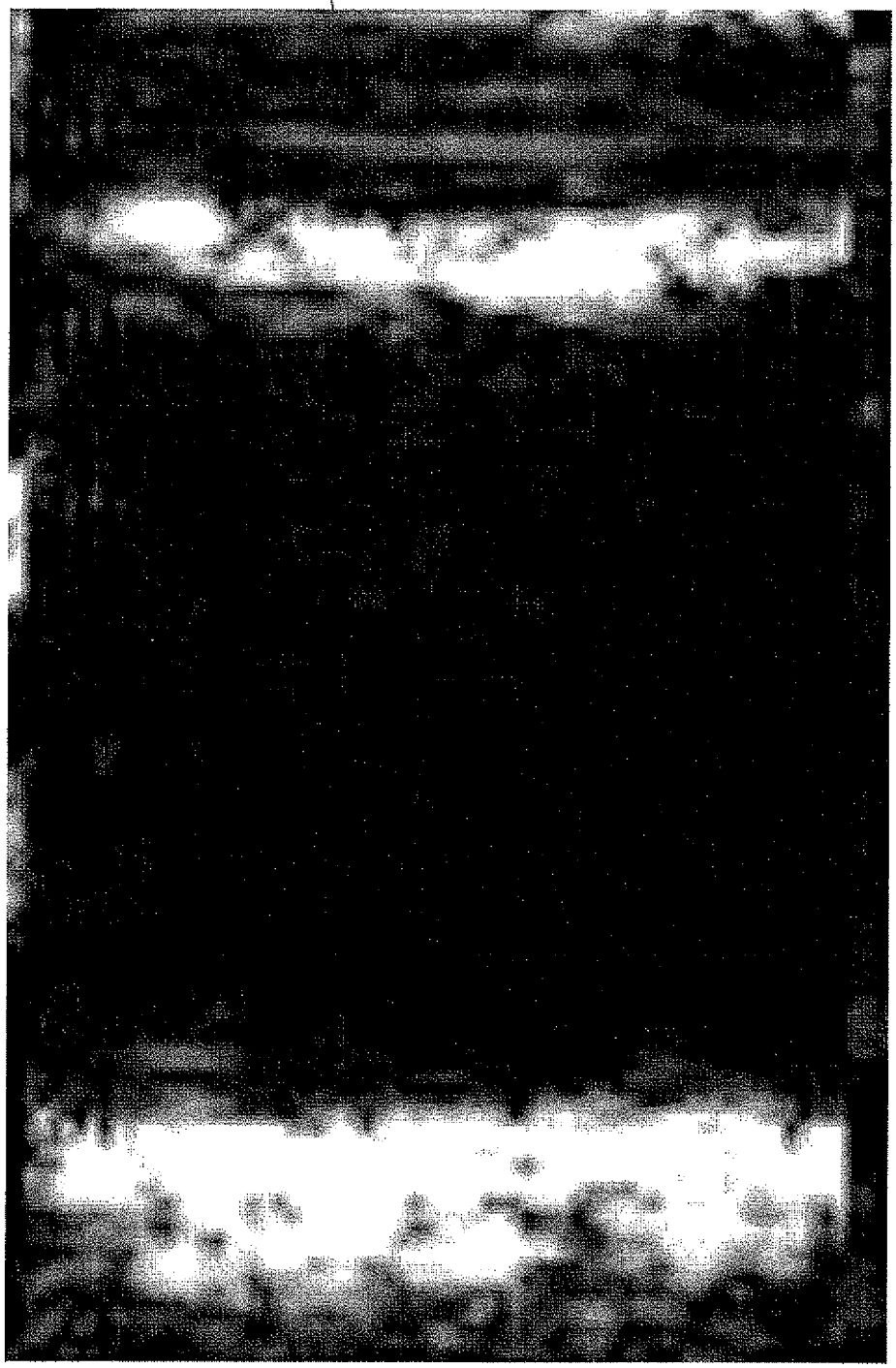
FIG. 7 is a view indicating another example of the longitudinal cross sectional image of the blood vessel displayed in the long-axis image display region of the monitoring display device of FIG. 1, which is different from that of FIG. 6, where the clarity of the intima-media complex of the blood vessel wall is relatively low.

On the other hand, a longitudinal cross sectional image of the blood vessel 20 may not be obtained with a high degree of clarity of the image of the intima-media complex IMC as shown in FIG. 6, in some cases, for instance, where the blood vessel 20 is curved, even when the ultrasonic probe 24 is located at the above-described predetermined measuring position PT1. In the case of FIG. 7, for example, the longitudinal cross sectional image of the blood vessel 20 has a low degree of clarity of the image of the intima-media complex IMC. In the longitudinal cross sectional image of FIG. 7 contrary to that of FIG. 6, a boundary between the lumen and the wall of the blood vessel 20 is discontinuous in the longitudinal direction of the blood vessel 20, for both the front wall portion $BR_F$ and the back wall portion $BR_B$, and the low echo band $BL_{IMC}$ of the intima-media complex IMC is almost invisible and unclear in the image. Where the longitudinal cross sectional blood vessel image is unclear with respect to the intima-media complex IMC as in the case of FIG. 7, the operator makes a fine positional adjustment of the ultrasonic probe 24, for example, to increase the clarity of the image of the intima-media complex IMC for both of the front wall portion $BR_F$ and the back wall portion $BR_B$. The blood vessel inspecting apparatus 22 according to the present embodiment has a control function to assist the operator in the fine positional adjustment. A major portion of this control function will be described by reference to FIG. 8.

Figure 8:
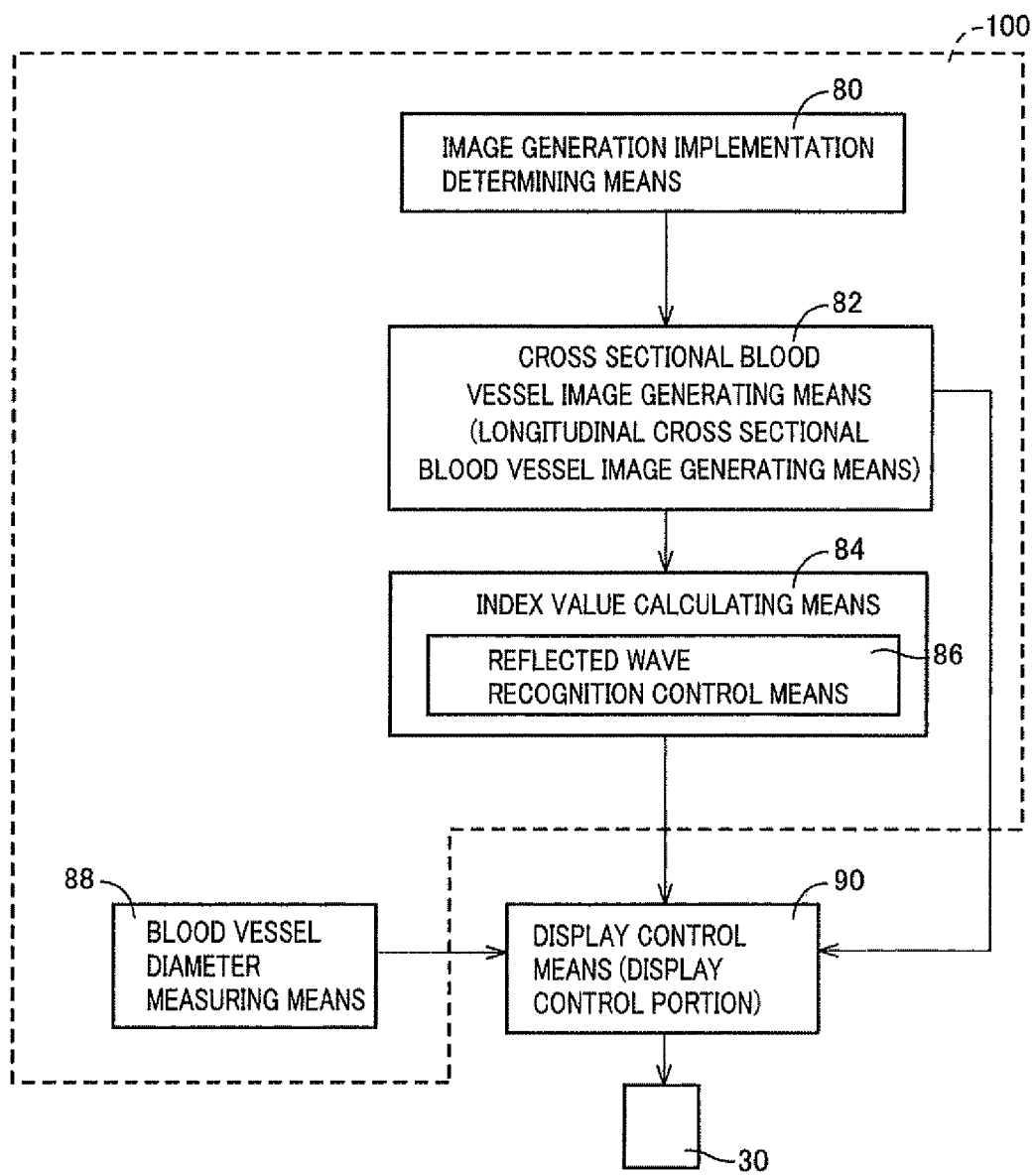
FIG. 8 is a functional block diagram for explaining major control functions of an electronic control apparatus included in the ultrasonic blood vessel inspecting apparatus of FIG. 1.

FIG. 8 is the functional block diagram for explaining major control functions of the blood vessel inspecting apparatus 22. As shown in FIG. 8, a blood vessel image evaluating portion 100 (shown in FIG. 1) incorporated in the electronic control device 28 is provided with an image generation implementation determining portion in the form of image generation implementation determining means 80, a cross sectional blood vessel image generating portion in the form of cross sectional blood vessel image generating means 82, an index value calculating portion in the form of index value calculating means 84, and a blood vessel diameter measuring portion in the form of blood vessel diameter measuring means 88.

The image generation implementation determining means 80 is configured to determine whether the ultrasonic probe 24 is operated to obtain ultrasonic images of the blood vessel 20, or not, namely, determine a moment of initiation and a moment of termination of the operation to obtain the ultrasonic images of the blood vessel 20.

Where the blood vessel inspecting apparatus 22 is provided with a switch operable to obtain the ultrasonic images of the blood vessel 20, for instance, the image generation implementation determining means 80 determines that the operation to obtain the above-described ultrasonic images is initiated, when the switch is turned on, and determines that the operation to obtain the above-described ultrasonic images is terminated, when the switch is turned off.

The cross sectional blood vessel image generating means 82 functions as longitudinal cross sectional blood vessel image generating means, and is configured to successively generate the longitudinal cross sectional image of the blood vessel 20 (longitudinal cross sectional blood vessel image) located below the skin of the live body 14, on the basis of a reflected wave signal $SG_{EC}$ of the ultrasonic wave generated from the ultrasonic probe 24 disposed on the skin of the live body. Specifically, the cross sectional blood vessel image generating means 82 successively generates the longitudinal cross sectional blood vessel images on the basis of reflected wave signal $SG_{EC}$ of the ultrasonic wave received by the long-axis ultrasonic detector array 24c successively and repeatedly. Described more specifically, the above-described longitudinal cross sectional image of the blood vessel 20 is an image as displayed in the long-axis image display region G3 indicated in FIG. 6 or 7, and is generated by the cross sectional blood vessel image generating means 82, in a B-mode method as generally known in the art.

Described in detail, during generating the longitudinal cross sectional blood vessel image, the cross sectional blood vessel image generating means 82 generates the above-described longitudinal cross sectional blood vessel image on the basis of the above-described reflected wave signal $SG_{EC}$ of the ultrasonic wave received by the long-axis ultrasonic detector array 24c. That is, the cross sectional blood vessel image generating means 82 scans and receives the reflected wave signal $SG_{EC}$ of the ultrasonic wave at a predetermined reflected wave reception time interval (line pitch) $PC_R$:v in the longitudinal direction of the long-axis ultrasonic detector array 24c, and generates the above-described longitudinal cross sectional blood vessel image on the basis of the received plurality of reflected wave signals $SG_{EC}$.

The cross sectional blood vessel image generating means 82 is further configured to function as transverse cross sectional blood vessel image generating means for successively generating a transverse cross sectional image of the blood vessel 20 (transverse cross sectional blood vessel image) to be displayed in the first short-axis image display region G1, on the basis of the reflected wave signals $SG_{EC}$ of the above-described ultrasonic wave successively and repeatedly received, by the first short-axis ultrasonic detector array 24a, and successively generating a transverse cross sectional image of the blood vessel 20 to be displayed in the second short-axis image display region G2, on the basis of the reflected wave signals $SG_{EC}$ of the above-described ultrasonic wave successively and repeatedly received by the second short-axis ultrasonic detector array 24b. For example, the cross sectional blood vessel image generating means 82 repeatedly generates the above-described longitudinal cross sectional blood vessel image and the above-described transverse cross sectional blood vessel images with a time period $T_A$ or longer which is predetermined to prevent blinking of the images displayed on the monitoring image display device 30, from a moment at which the image generation implementation determining means 80 determines the initiation of the operation to obtain the above-described ultrasonic images, to a moment at which the image generation implementation determining means 80 determines the termination of the operation.

The index value calculating means 84 is configured to calculate index values indicative of the clarity of the image of the intima-media complex IMC of the blood vessel 20 existing within the above-described longitudinal cross sectional blood vessel image generated by the cross sectional blood vessel image generating means 82. For instance, the index value calculating means 84 calculates the index values each time the cross sectional blood vessel image generating means 82 generates the longitudinal cross sectional blood vessel image. Described more specifically, the index value is calculated for each of the front wall portion $BR_F$ and back wall portion $BR_B$ within the above-described longitudinal cross sectional blood vessel image. Namely, the index value calculating means 84 calculates a front wall portion image clarity index value $XCR_F$ indicative of the degree of clarity of the image of the intima-media complex IMC of the front wall portion $BR_F$ existing within the above-described longitudinal cross sectional blood vessel image, and a back wall portion image clarity index value $XCR_B$ indicative of the degree of clarity of the image of the intima-media complex IMC of the back wall portion $BR_B$ existing within the above-described longitudinal cross sectional blood vessel image. To calculate those front wall portion image clarity index value $XCR_F$ and back wall portion image clarity index value $XCR_B$, the index value calculating means 84 is provided with a reflected wave recognition control portion in the form of reflected wave recognition control means 86. In this respect, it is noted that the degree of clarity of the image of the above-described intima-media complex IMC means a degree in which the low echo band $BL_{IMC}$ and a high echo band representative of the intima-media complex IMC in the above-described longitudinal cross sectional blood vessel image can be recognized continuously in the longitudinal direction of the blood vessel 20, since the intima-media complex IMC extends in the longitudinal direction of the blood vessel 20. It is further confirmed here that the above-described front wall portion image clarity index value $XCR_F$ and the above-described back wall portion image clarity index value $XCR_B$ are collectively considered to be an index value indicative of the degree of clarity of the image representative of the above-described intima-media complex IMC.

Figure 9:
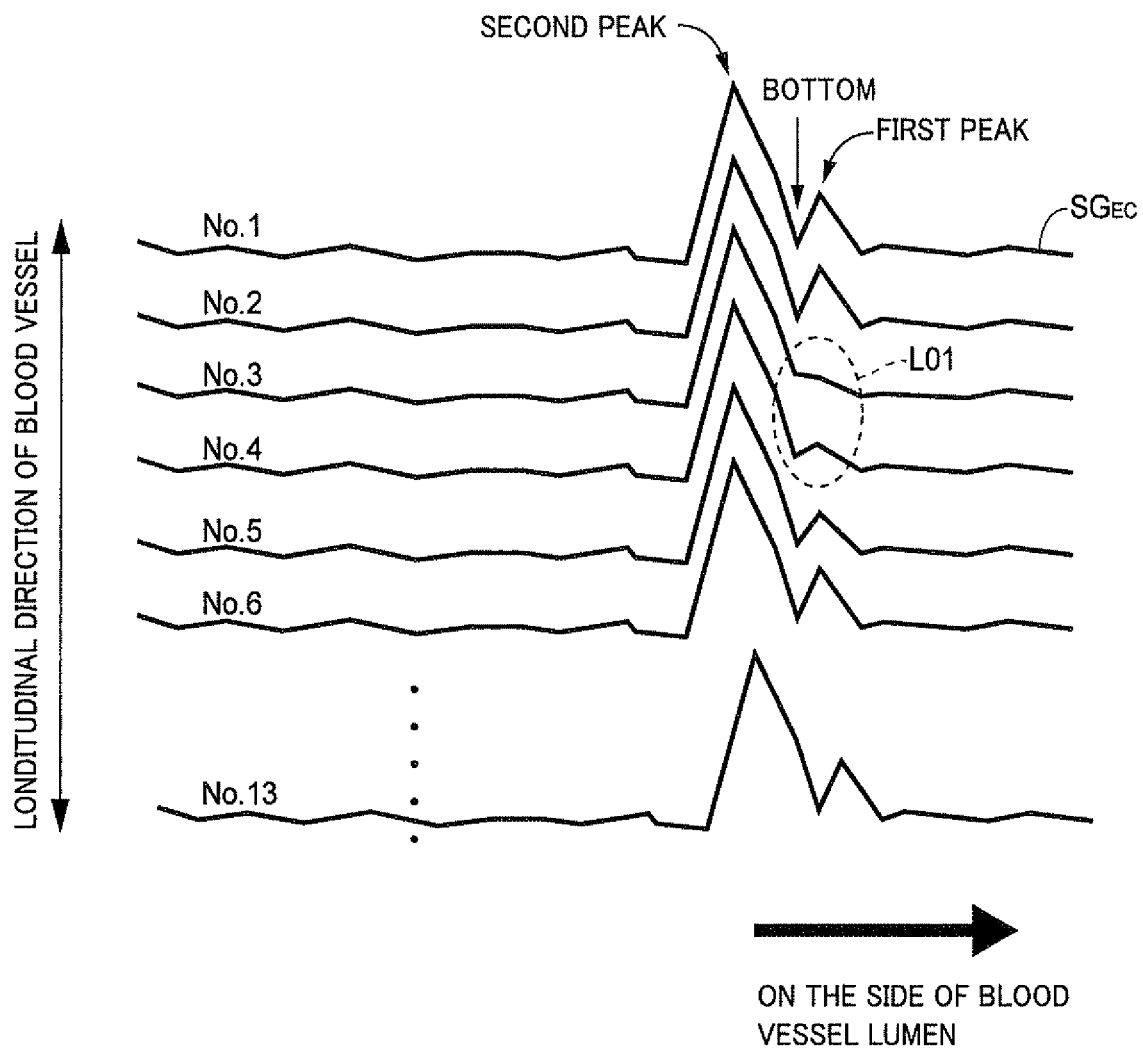
FIG. 9 is a view illustrating a plurality of reflected wave signals received by a long-axis ultrasonic detector array of FIG. 2 at respective different positions in the longitudinal direction of the blood vessel.

The reflected wave recognition control means 86 is configured to obtain the plurality of reflected wave signals $SG_{EC}$ received by the blood vessel cross sectional image generating means 82 to generate the above-described longitudinal cross sectional blood vessel image, each time the cross sectional blood vessel image generating means 82 generates the longitudinal cross sectional blood vessel image, for example. The reflected wave recognition control means 86 obtains the reflected wave signal $SG_{EC}$ from the cross sectional blood vessel image generating means 82, for instance. The above-described plurality of reflected wave signals $SG_{EC}$ for generating one longitudinal cross sectional blood vessel image are those received by the long-axis ultrasonic detector array 24c at mutually different positions of reception in the longitudinal direction of the blood vessel. That is, the reflected wave recognition control means 86 obtains the plurality of reflected wave signals $SG_{EC}$ received by the long-axis ultrasonic detector array 24c at the respective different positions in the longitudinal direction of the blood vessel, as indicated in FIG. 9 by way of example.

Figure 10:
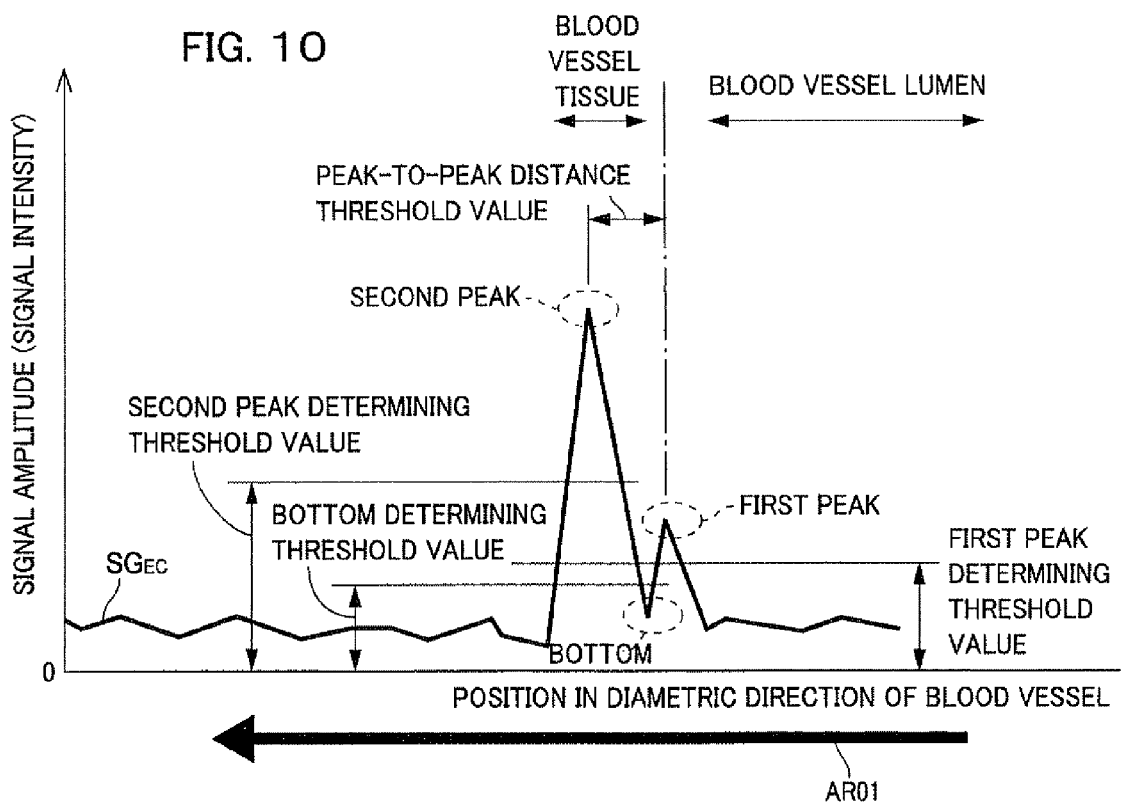
FIG. 10 is a view indicating one of the plurality of reflected wave signals indicated in FIG. 9, in a two-dimensional coordinate system wherein an amplitude of the signal is taken along a vertical axis while the position of the blood vessel in its diametric direction is taken along a horizontal axis.

The reflected wave recognition control means 86 implements a reflected wave recognition control, for each of the plurality of reflected wave signals $SG_{EC}$ obtained as described above, and for each of the above-described front wall portion $BR_F$ and back wall portion $BR_B$, to detect according to a relationship as indicated in FIG. 10 between the amplitude $AM_{SG}$ of the reflected wave signals $SG_{EC}$ and a position $PT_R$ in a diametric direction of the blood vessel 20: a first peak PK1 of each reflected wave signal $SG_{EC}$ at which the amplitude $AM_{SG}$ of the reflected wave signal $SG_{EC}$ is larger than a predetermined first peak determining threshold value $LT1_{PK}$ as indicated in FIG. 10; a bottom BTM of the reflected wave signal $SG_{EC}$ which is generated at a position of the blood vessel 20 located outwardly of the position of generation of the first peak PK1 in the diametric direction of the blood vessel 20 and at which the amplitude $AM_{SG}$ is smaller than a predetermined bottom determining threshold value $LT_{BTM}$, as also indicated in FIG. 10; and a second peak PK2 of the reflected wave signal $SG_{EC}$ which is generated at a position of the blood vessel 20 located outwardly of the position of generation of the first peak PK1 in the diametric direction of the blood vessel 20 but located within a spacing distance from the position of generation of the first peak PK1 not exceeding a predetermined peak-to-peak distance threshold value $LT_{SP}$, with the bottom BTM being located therebetween, and at which the amplitude $AM_{SG}$ is larger than a predetermined second peak determining threshold value $LT2_{PK}$, as also indicated in FIG. 10. This reflected wave recognition control will be described more specifically by reference to FIG. 10.

FIG. 10 is the view indicating a portion of one reflected wave signal $SG_{EC}$, which portion corresponds to the above-described front wall portion $BR_F$ or back wall portion $BR_B$, in a two-dimensional coordinate system wherein the amplitude $AM_{SG}$ of the reflected wave signal $SG_{EC}$ (signal intensity $AM_{SG}$) is taken along a vertical axis while a position $PT_R$ of the blood vessel 20 in its diametric direction is taken along a horizontal axis. Where the portion of the reflected wave signal $SG_{EC}$ indicated in FIG. 10 corresponds to the front wall portion $BR_F$, for example, an arrow-headed line AR01 in FIG. 10 corresponds to an arrow-headed line AR02 in the longitudinal cross sectional blood vessel image of FIG. 11. Or where the portion of the reflected wave signal $SG_{EC}$ indicated in FIG. 10 corresponds to the back wall portion $BR_B$, for example, an arrow-headed line AR01 in FIG. 10 corresponds to an arrow-headed line AR03 in FIG. 11. In the example of FIG. 10, the first peak PK1, bottom BTM and second peak PK2 of the reflected wave signal $SG_{EC}$ have a triangular waveform of an actuate angle respectively. However, any of the first peak PK1, bottom BTM and second peak PK2 may have a trapezoidal waveform having an almost flat segment, rather than the triangular waveform.

The reflected wave recognition control means 86 initially recognizes a portion of the reflected wave signal $SG_{EC}$ which corresponds to the lumen of the blood vessel. For example, the reflected wave recognition control means 86 may recognize this portion from the transverse cross sectional images (short-axis images) of the blood vessel 20, or may recognize an intermediate position of the relevant portion of the reflected wave signal $SG_{EC}$ representative of each of the front wall portion $BR_F$ and the back wall portion $BR_B$, as the blood vessel lumen. In the present embodiment, the above-described reflected wave recognition control is implemented with respect to the reflected wave signals $SG_{EC}$ received within a predetermined observation range AOB (indicated in FIG. 11) of the blood vessel 20 in its longitudinal direction, as described below, so that the above-indicated portion corresponding to the blood vessel lumen may be recognized with respect to those of the plurality of reflected wave signals $SG_{EC}$ used to generate the above-described longitudinal cross sectional blood vessel image, which are received within the observation range AOB.

In the above-described reflected wave recognition control, the reflected wave recognition control means 86 then recognizes the amplitude $AM_{SG}$ of the reflected wave signal $SG_{EC}$ in the diametrically outward direction of the blood vessel from its lumen toward its outer layer as indicated by the arrow-headed line AR01 in FIG. 10, at one of the front wall portion $BR_F$ and back wall potion $BR_B$, to detect, as the first peak PK1, a maximal point of the signal amplitude $AM_{SG}$ which is larger than the above-described first peak determining threshold value $LT1_{PK}$. Subsequently, the reflected wave recognition control means 86 detects, as the bottom BTM, a minimal point of the signal amplitude $AM_{SG}$ which is located outwardly of the position of generation of the first peak PK1 in the diametric direction of the blood vessel 20 (position along the horizontal axis of the coordinate system of FIG. 10) and at which the amplitude $AM_{SG}$ is smaller than the above-described bottom determining threshold value $LT_{BTM}$. Then, the reflected wave recognition control means 86 detects, as the second peak PK2, a maximal point of the signal amplitude $AM_{SG}$ which is generated at a position of the blood vessel 20 located outwardly of the position of generation of the first peak PK1 in the diametric direction of the blood vessel 20 but located within a spacing distance from the position of generation of the first peak PK1 not exceeding the above-described predetermined peak-to-peak distance threshold value $LT_{SP}$, with the bottom BTM being located therebetween, and at which the signal amplitude $AM_{SG}$ is larger than the predetermined second peak determining threshold value $LT2_{PK}$. After the first peak PK1, bottom BTM and second peak PK2 have been detected at one of the front wall portion $BR_F$ and back wall portion $BR_B$, the reflected wave recognition control means 86 repeats the same detection at the other of the front wall portion $BR_F$ and back wall portion $BR_B$, for the same reflected wave signal $SG_{EC}$. The reflected wave recognition control means 86 implements the above-described reflected wave recognition control at both of the front wall portion $BR_F$ and back wall portion $BR_B$, for all of the plurality of reflected wave signals $SG_{EC}$.

Figure 11:
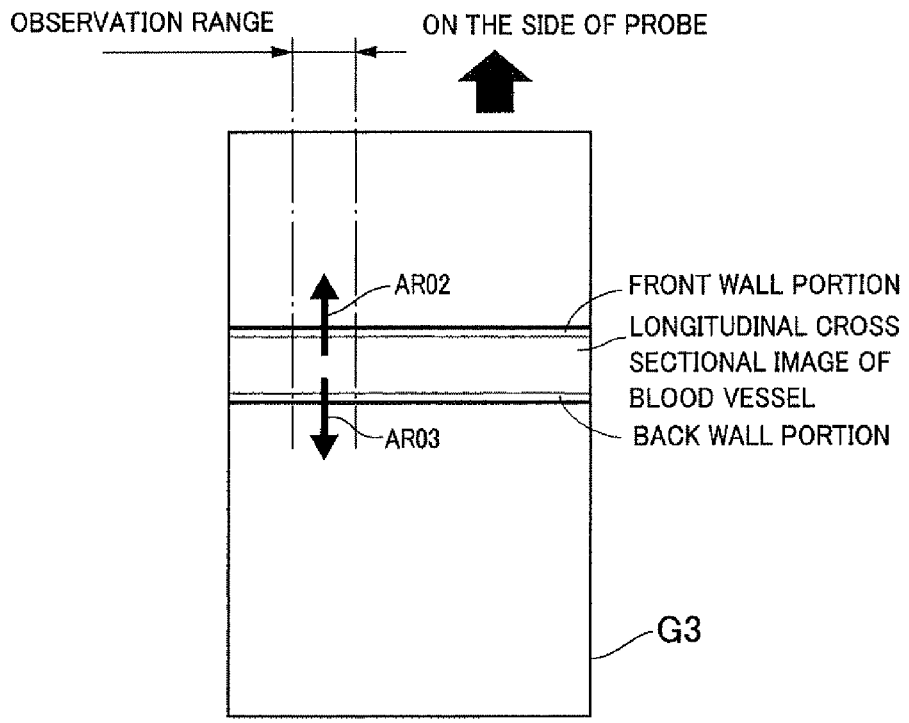
FIG. 11 is a view schematically illustrating the longitudinal cross sectional image of the blood vessel displayed in the long-axis image display region of the monitoring image display device of FIG. 1, for explaining a relationship of the longitudinal cross sectional image of the blood vessel with the view of FIG. 10.
Figure 12:
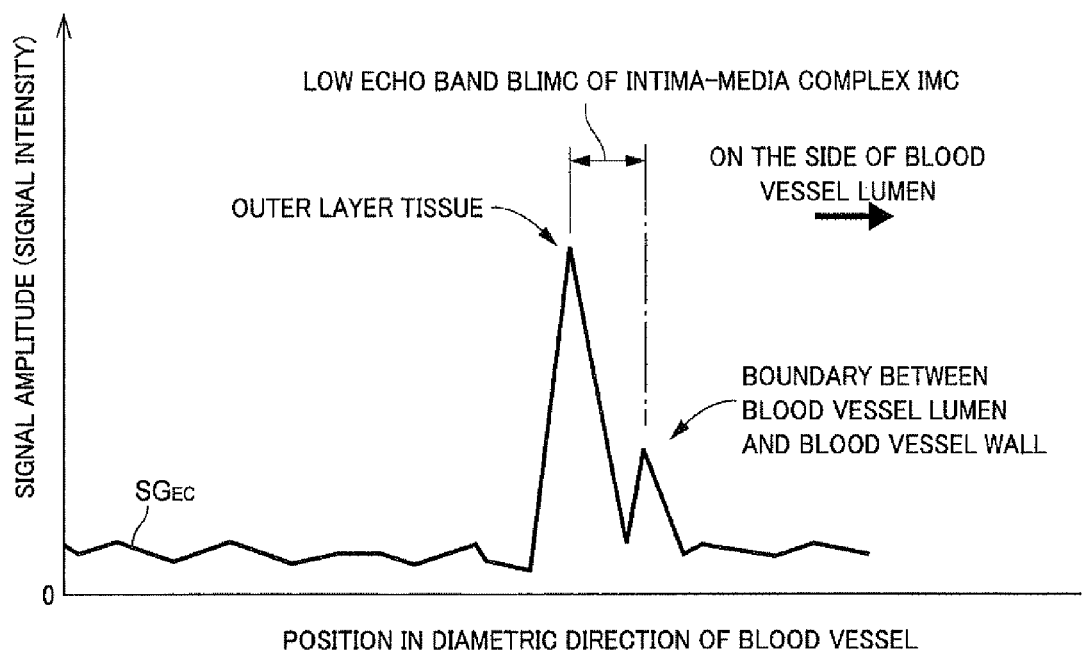
FIG. 12 is a view indicating the same reflected wave signal as indicated in FIG. 10, for explaining a tissue of the blood vessel as represented by this reflected wave signal.

In the above-described reflected wave recognition control, the amplitude $AM_{SG}$ of the reflected wave signal $SG_{EC}$ is compared with the above-described first peak determining threshold value $LT1_{PK}$, the above-described bottom determining threshold value $LT_{BTM}$ and the above-described second peak determining threshold value $LT2_{PK}$. However, the above-described signal amplitude $AM_{SG}$ compared with the threshold values may be replaced by any other parameter representative of a magnitude of the reflected wave signal $SG_{EC}$ relating to the above-described longitudinal cross sectional blood vessel image, such as a brightness value obtained by conversion of the above-described signal amplitude $AM_{SG}$, which brightness value is used to display the longitudinal cross sectional blood vessel image (B-mode long-axis image). The above-described first peak determining threshold value $LT1_{PK}$, the above-described bottom determining threshold value $LT_{BTM}$ and the above-described second peak determining threshold value $LT2_{PK}$ are predetermined by experimentation, to permit visual recognition as respective mutually different ultrasonic image patterns respectively corresponding to the first peak PK1, bottom BTM and second peak PK2. The above-described bottom determining threshold value $LT_{BTM}$ is predetermined to be smaller than the above-described first peak determining threshold value $LT1_{PK}$ and the above-described second peak determining threshold value $LT2_{PK}$. In the example of FIG. 10, the second peak PK2 is higher than the first peak PK1. Since the second peak PK2 may be lower than the first peak PK1, however, the above-described first peak determining threshold value $LT1_{PK}$ and the above-described second peak determining threshold value $LT2_{PK}$ are suitably determined without a specific limitation about sizes of the first and second peak determining threshold values, and may be different from or equal to each other. As indicated in FIG. 12, a portion of the reflected wave signal $SG_{EC}$ which is located between the first peak PK1 and the second peak PK2 and which includes the bottom BTM is recognized as the above-described low echo band $BL_{IMC}$ of the intima-media complex IMC, in the above-described longitudinal cross sectional blood vessel image, so that the above-described peak-to-peak distance threshold value $LT_{SP}$ is predetermined by experimentation on the basis of the thickness of the intima-media complex IMC of the live body, for example. Although the reflected wave recognition control means 86 may be configured to implement the above-described reflected wave recognition control for all of the plurality of reflected wave signals $SG_{EC}$ used to generate the above-described longitudinal cross sectional blood vessel image, the reflected wave recognition control means 86 in the present embodiment implements the above-described reflected wave recognition control for only the reflected wave signals $SG_{EC}$ received within the predetermined observation range AOB of the blood vessel 20 in its longitudinal direction, as indicated in FIG. 11, in order to reduce a load of arithmetic operation. This observation range AOB, which corresponds to a portion of the longitudinal dimension of the long-axis ultrasonic detector array 24c, may be either a constant value or a variable which can be set by the operator, and is predetermined by experimentation so as to permit determination of the degree of clarity of the intima-media complex IMC in the above-described longitudinal cross sectional blood vessel image.

FIG. 10 indicates the example of the reflected wave signal $SG_{EC}$ whose first peak PK1, bottom BTM and second peak PK2 are all detected by implementation of the above-described reflected wave recognition control. However, some of the reflected wave signals $SG_{EC}$ may not have any one or all of the first peak PK1, bottom BTM and second peak PK2. In view of this possibility, the reflected wave recognition control means 86 stores in a memory a number $QL_{SG}$ of the reflected wave signals $SG_{EC}$ received within the above-described observation range AOB, all of the first peak PK1, bottom BTM and second peak PK2 of which have been detected by implementation of the above-described reflected wave recognition control, for each of the front wall portion $BR_F$ and the back wall portion $BR_B$. This number $QL_{SG}$ is referred to as "peak recognized line number $QL_{SG}$". In the example of FIG. 9, the number of the reflected wave signals $SG_{EC}$ (number of lines) for which the above-described reflected wave recognition control is implemented is equal to 13 (=observation range AOB/reflected, wave signal reception time interval $PC_{RV}$). In this case, the reflected wave recognition control means 86 implements the above-described reflected wave recognition control for all of the 13 reflected wave signals $SG_{EC}$, for each of the front wall portion $BR_F$ and the back wall portion $BR_B$. Where the first peak PK1 cannot be detected for the No. 3 and No. 4 reflected wave signals $SG_{EC}$, as indicated by a broken line L01, these two reflected wave signals $SG_{EC}$ are not included in the peak recognized line number $QL_{SG}$, so that "11"(=13−2) is stored in the memory as the peak recognized line number $QL_{SG}$.

After the reflected wave recognition control means 86 implements the above-described reflected wave recognition control for the plurality of reflected wave signals $SG_{EC}$ received within the above-described observation range AOS, the index value calculating means 84 calculates the above-described front wall portion image clarity index value $XCR_F$, on the basis of the number $QL_{SG}$ (peak recognized line number $QL_{SG}$) of the reflected wave signals $SG_{EC}$ all of the above-described first peak PK1, bottom BTM and second peak PK2 of which have been detected by the above-described reflected wave recognition control implemented by the reflected wave recognition control means 86 for the front wall portion $BR_F$. Then, the index value calculating means 84 calculates the above-described back wall portion image clarity index value $XCR_B$, on the basis of the number $QL_{SG}$ (peak recognized line number $QL_{SG}$) of the reflected wave signals $SG_{EC}$ all of the above-described first peak PK1, bottom BTM and second peak PK2 of which have been detected by the above-described reflected wave recognition control implemented by the reflected wave recognition control means 86 for the back wall portion $BR_B$. Described more specifically, the index value calculating means 84 calculates the above-described front wall portion image clarity index value $XCR_F$; that is, the front wall portion score $XCR_F$, according to the following Equation (1), and the above-described back wall portion image clarity index value $XCR_B$, that is, the back wall portion score $XCR_B$, according to the following Equation (2). In the following Equations (1) and (2), "$XCR_F$", "$XCR_B$", "$QLF_{SG}$", "$QLB_{SG}$", "$PC_{RV}$", and "AOB" respectively represent: the above-described front wall portion score $XCR_F$; the above-described back wall portion score $XCR_B$; the peak recognized line number $QL_{SG}$ for the front wall portion $BR_F$; the peak recognized line number $QL_{SG}$ for the back wall portion $BR_B$; the above-described reflected wave signal reception time interval (line pitch) $PC_{RV}$; and the above-described observation range (observation area width) AOB.

$$XCR_F=(QLF_{SG}\times PC_{RV})/AOB\times 100 \qquad (1)$$

$$XCR_B=(QLB_{SG}\times PC_{RV})/AOB\times 100 \qquad (2)$$

Thus, the index value calculating means 84 calculates the above-described front wall portion image clarity index value $XCR_F$ and the above-described back wall portion image clarity index value $XCR_B$. It will be understood from the above-indicated Equations (1) and (2) that each of the image clarity index values $XCR_F$ and $XCR_B$ is a relative value which changes within a range between 0 and 100. Each time the index value calculating means 84 calculates the image clarity index values $XCR_F$ and $XCR_B$, the monitoring image display device 30 displays the front wall portion image clarity index value $XCR_F$ and the back wall portion image clarity index value $XCR_B$, as indicated by a two-dot chain line L02 in FIG. 13, together with the above-described longitudinal cross sectional blood vessel image and the above-described transverse cross sectional blood vessel images. Described more specifically by reference to FIG. 14 which is the enlarged view of the portion enclosed by the two-dot chain line L02 in FIG. 13, the index value calculating means 84 commands the monitoring image display device 30 to display the front wall portion image clarity index value $XCR_F$ and the back wall portion image clarity index value $XCR_B$, not only as numerical values, but also as two images or two graphic figures which are continuously variable according to the index values $XCR_F$, $XCR_B$ and which are comparable with each other. In the example of FIG. 14, the front wall portion image clarity index value $XCR_F$ and back wall portion image clarity index value $XCR_B$ are indicated by respective two graphic figures in the form of a pair of sectors (black areas shown in FIG. 14), being symmetry with respect to a common straight line, center angles of which increase with an increase of the respective index values, so that the surfaces areas of the two sectors accordingly increase. When each of the index values $XCR_F$, $XCR_B$ is equal to the maximum value of 100, the corresponding sector takes the form of a semicircle. When both of the index values $XCR_F$, $XCR_B$ are equal to the maximum value, the above-indicated two semicircles cooperate to form a complete circle.

The blood vessel diameter measuring means 88 is configured to measure the blood vessel lumen diameter $d_1$ in a non-invasion manner, on the basis of the above-described longitudinal cross sectional blood vessel image. Described more specifically, the blood vessel diameter measuring means 88 measures a blood vessel lumen diameter da at rest (rest-time diameter $d_a$) before releasing of the blood vessel 20 from blood flow obstruction, for measuring the diameter change ratio of the blood vessel 20 (dilatation ration R of the blood vessel lumen diameter $d_1$) after releasing of the blood vessel 20 from the blood flow obstruction, for implementing the FMD evaluation. The blood vessel diameter measuring means 88 is further configured to measure the blood vessel lumen diameter $d_1$ from time to time during a predetermined blood vessel diameter measuring time period TIME1 after releasing of the blood vessel 20 from the blood flow obstruction, and to calculate the diameter change ratio R of the blood vessel 20 from time to time, on the basis of the measured blood vessel lumen diameter $d_1$ and the above-described rest-time diameter $d_a$, for implementing the FMD evaluation. For instance, the blood vessel diameter measuring means 88 chronologically continuously measures the blood vessel lumen diameter $d_1$ during the above-described blood vessel diameter measuring time period TIME1 while the blood vessel lumen diameter $d_1$ varies after releasing of the blood vessel from the blood flow obstruction, as indicated in FIG. 5. Alternatively, the blood vessel diameter measuring means 88 may measure the blood vessel lumen diameter $d_1$ at one, two or more predetermined measuring point or points of time with respect to the moment of releasing of the blood vessel from the blood flow obstruction. Each predetermined measuring point of time is a point at which the blood vessel lumen diameter $d_1$ is estimated to have the almost largest value $d_{MAX}$, and is obtained in advance by experimentation. The above-described blood vessel diameter measuring time period TIME1 during which the blood vessel lumen diameter $d_1$ is to be measured to detect its largest value $d_{MAX}$ after releasing of the blood vessel from the blood flow obstruction is determined by experimentation with respect to the moment of releasing of the blood vessel from the blood flow obstruction, and is stored in the blood vessel diameter measuring means 88. As indicated in FIG. 5, this time period TIME1 includes the point of time (t3) at which the blood vessel lumen diameter $d_1$ reaches the largest value $d_{MAX}$ and starts from the moment (point of time t1) at which the blood vessel is released from the blood flow obstruction. Thus, the blood vessel diameter measuring means 88 measures the maximum value $d_{MAX}$ (maximum lumen diameter) of the blood vessel 20 after releasing of the blood vessel 20 from the blood flow obstruction.

The blood vessel diameter measuring means 88 is further configured to calculate a maximum change ratio $R_{MAX}$ of the diameter of the blood vessel 20 after releasing of the blood vessel from the blood flow obstruction with respect to the above-described rest-time diameter $d_a$ after expiration of the above-described blood vessel diameter measuring time period TIME1, namely, to calculate, as a blood vessel dilatation ratio evaluating value (a % FMD value), the maximum value $R_{MAX}(\%)$ [$=100\times(d_{MAX}-d_a)/d_a$] of the diameter change ratio (dilatation ratio R) of the blood vessel 20 with respect to the rest-time diameter $d_a$ after releasing of the blood vessel 20 from the blood flow obstruction. The monitoring image display device 30 displays the calculated blood vessel dilatation ratio evaluating value $R_{MAX}$.

The index value calculating means 84 has, in addition to the above-described function, a function of calculating the front wall portion image clarity index value $XCR_F$ and back wall portion image clarity index value $XCR_B$ at the time of measurement of the above-described rest-time diameter $d_a$, and the front wall portion image clarity index value $XCR_F$ and back wall portion image clarity index value $XCR_B$ at the time of measurement of the above-described maximum diameter $d_{MAX}$ after the blood vessel releasing from the blood flow obstruction. Then, the index value calculating means 84 calculates an index value $XCR_{FMD}$ indicative of a degree of reliability of the maximum diameter change ratio (blood vessel dilatation ratio evaluating value) $R_{MAX}$ after the blood vessel releasing from the blood flow obstruction, with respect to the rest-time diameter $d_a$ of the blood vessel 20 calculated by the blood vessel diameter measuring means 88, namely, calculates the FMD reliability index value $XCR_{FMD}$, on the basis of the front wall portion image clarity index value $XCR_F$ and back wall portion image clarity index value $XCR_B$ at the time of measurement of the rest-time diameter $d_a$, and the front wall portion image clarity index value $XCR_F$ and back wall portion image clarity index value $XCR_B$ at the time of measurement of the maximum diameter $d_{MAX}$. For example, the index value calculating means 84 calculates, as a rest-time diameter measurement score XCR1, an average of the front wall portion image clarity index value $XCR_F$ and back wall portion image clarity index value $XCR_B$ at the time of measurement of the above-described rest-time diameter $d_a$, and calculates, as a maximum diameter measurement score $XCR2$, an average of the front wall portion image clarity index value $XCR_F$ and back wall portion image clarity index value $XCR_B$ at the time of measurement of the above-described maximum diameter $d_{MAX}$. Then, the index value calculating means 88 calculates the above-described FMD reliability index value $XCR_{FMD}$ on the basis of the rest-time diameter measurement score $XCR1$ and the maximum diameter measurement score $XCR2$ and according to the following Equation (3). The monitoring image display device 30 displays the calculated FMD reliability index value $XCR_{FMD}$, together with the above-described blood vessel dilatation ratio evaluating value $R_{MAX}$. This FMD reliability index value $XCR_{FMD}$ is an index value indicative of the reliability of the above-described blood vessel dilatation ratio evaluating value $R_{MAX}$, as described above, in other words, an index value indicative of the accuracy of measurement of the blood vessel dilation ratio evaluating value $R_{MAX}$. Accordingly, the accuracy of measurement of the above-described blood vessel dilatation ratio evaluating value $R_{MAX}$ increases with an increase of the FMD reliability index value $XCR_{FMD}$.

$$XCR_{FMD} = (XCR1 + XCR2)/2 \qquad (3)$$

Figure 13:
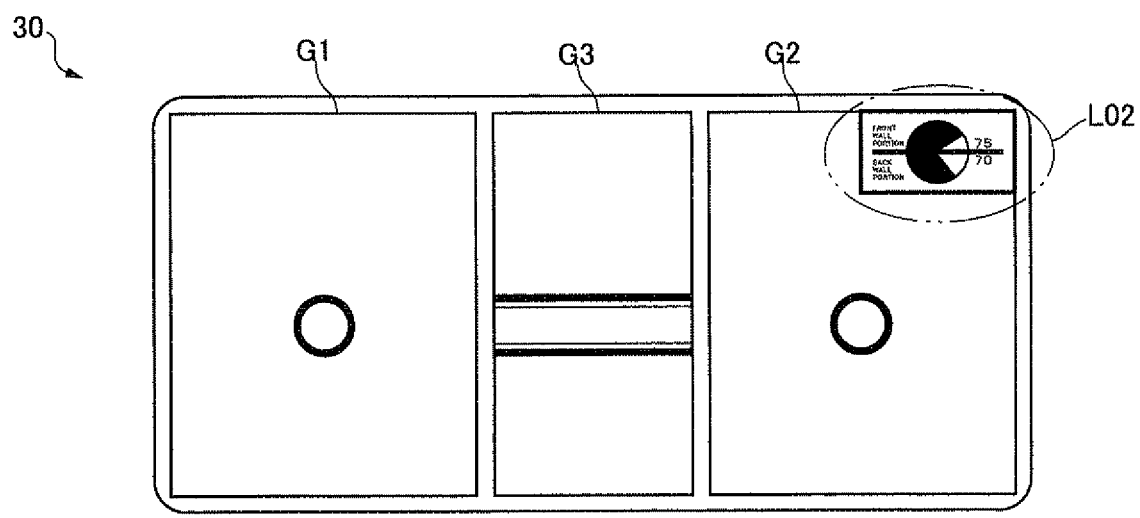
FIG. 13 is a view illustrating a longitudinal cross sectional image, a transverse cross sectional image of the blood vessel, a front wall portion image clarity index value and a back wall portion image clarity index value, which are displayed on the monitoring image display device of FIG. 1.
Figure 14:
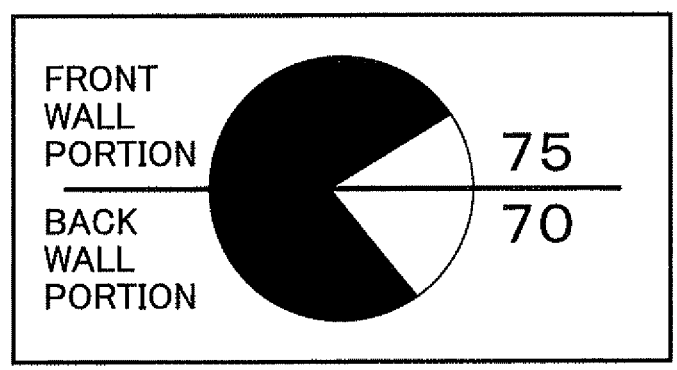
FIG. 14 is an enlarged view of a portion of the monitoring image display device in which the front wall portion image clarity index value and the back wall portion image clarity index value are indicated.

Display control means 90 (display control portion 90) provided in the electronic control device 28 is configured to command the monitoring image display device 30 to display from time to time the above-described longitudinal cross sectional blood vessel image and the above-described transverse cross sectional images which are generated by the cross sectional blood vessel image generating means 82, and to display from time to time the numerical values and graphic figures (in the form of sectors) indicative of the front wall portion image clarity index value $XCR_F$ and back wall portion image clarity index value $XCR_B$ which are calculated by the index value calculating means 84, as indicated in FIGS. 13 and 14.

The display control means 90 is further configured to command the monitoring image display device 30 to display the blood vessel dilatation ratio evaluating value $R_{MAX}$ and the above-described FMD reliability index value $XCR_{FMD}$ when the FMD evaluation is implemented, that is, when the blood vessel diameter measuring means 88 calculates the blood vessel dilatation ratio evaluating value $R_{MAX}$.

Figure 15:
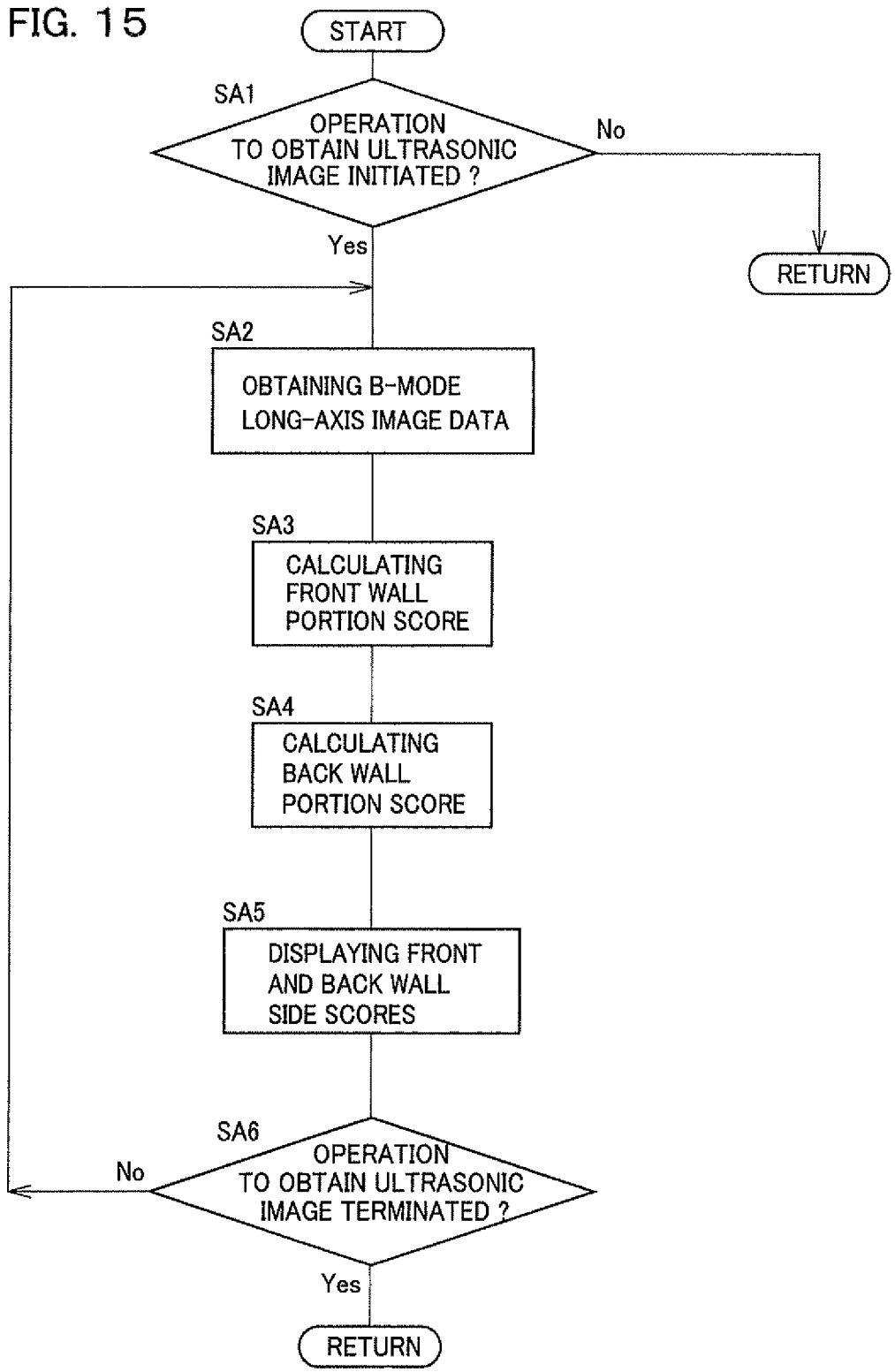
FIG. 15 is a flow chart illustrating a major control operation of the electronic control device of FIG. 8, namely, a control operation performed according to the first embodiment to generate the longitudinal cross sectional image of the blood vessel and to calculate the index values indicative of the clarity of the image of the intima-media complex of the blood vessel.

FIG. 15 is a flow chart illustrating a major control operation of the blood vessel inspecting apparatus 22 (electronic control device 28), namely, a control operation to generate the above-described longitudinal cross sectional blood vessel image and to calculate the index values indicative of the degree of clarity of the image of the intima-media complex IMC of the blood vessel 20. This control operation illustrated in FIG. 15 is performed alone, or concurrently with other control operation or operations.

Initially, step SA1 ("step" being hereinafter omitted) corresponding to the image generation implementation determining means 80 is implemented to determine whether the operation to obtain the ultrasonic image of the blood vessel 20 is initiated or not. If an affirmative determination is obtained in SA1, that is, if the operation to obtain the above-described ultrasonic image is initiated, the control flow goes to SA2. If a negative determination is obtained in SA1, the control operation of the flow chart of FIG. 15 is terminated.

In SA2 corresponding to the cross sectional blood vessel image generating means 82, the long-axis ultrasonic detector array 24c scans and receives the reflected wave signals $SG_{EC}$ of the ultrasonic wave in its longitudinal direction at the predetermined reflected wave reception time interval $PC_{RV}$. The received plurality of reflected wave signals $SG_{EC}$, namely, B-mode long-axis image data are stored in a memory device of the electronic control device 28, and the above-described longitudinal cross sectional blood vessel image is generated on the basis of the received plurality of reflected wave signals $SG_{EC}$.

In SA3 corresponding to the index value calculating means 84 and the reflected wave recognition control means 86, the above-described reflected wave recognition control is implemented for each of the reflected wave signals $SG_{EC}$ received within the above-described observation range AOB for the front wall portion $BR_F$. Then, the above-described front wall portion image clarity index value (front wall portion score) $XCR_F$ is calculated on the basis of the number $QL_{SG}$ ($QLF_{SG}$) of the reflected wave signals $SG_{EC}$ all of the above-described first peak PK1, bottom BTM and second peak PK2 of which have been detected by implementation of the above-described reflected wave recognition control for the front wall portion $BR_F$.

In SA4 corresponding to the index value calculating means 84 and the reflected wave recognition control means 86, the above-described reflected wave recognition control is implemented for reach of the reflected wave signals $SG_{EC}$ received within the above-described observation range AOB for the back wall portion $BR_B$. Then, the above-described back wall portion image clarity index value (back wall portion score) $XCR_B$ is calculated on the basis of the number $QL_{SG}$ ($QLB_{SG}$) of the reflected wave signals $SG_{EC}$ all of the above-described first peak PK1, bottom BTM and second peak PK2 of which have been detected by implementation of the above-described reflected wave recognition control for the back wall portion $BR_F$.

In SA5 corresponding to the display control means 90, the above-described longitudinal cross sectional blood vessel image generated in the above-described SA2, and the above-described front wall portion score $XCR_F$ and back wall portion score $XCR_B$ calculated in the above-described SA3 and SA4 respectively are displayed in a real-time fashion on the monitoring image display device 30, as indicated in FIGS. 13 and 14. In the example of FIG. 14, the front wall portion score $XCR_F$ and back wall portion score $XCR_B$ are displayed as the numerical values which change within the range between 0 and 100, and as the pair of sectors which cooperate to form a complete circle when both of the front wall portion score $XCR_F$ and back wall portion score $XCR_B$ are equal to the maximum value of 100.

In SA6 corresponding to the image generation implementation determining means 80, a determination as to whether the operation to obtain the ultrasonic image of the blood vessel 20 is terminated or not. If an affirmative determination is obtained in SA6, namely if the operation to obtain the above-described ultrasonic image is terminated, the control operation of the flow chart of FIG. 15 is terminated. If a negative determination is obtained in SA6, namely, if the control operation to obtain the above-described ultrasonic image is continued, the control flow goes back to the SA2. Accordingly, the steps SA2 through SA5 are repeatedly implemented during a time period between the moments of initiation and termination of the control operation to obtain the above-described ultrasonic image. For example, those steps are repeatedly implemented with an extremely short cycle time.

Figure 16:
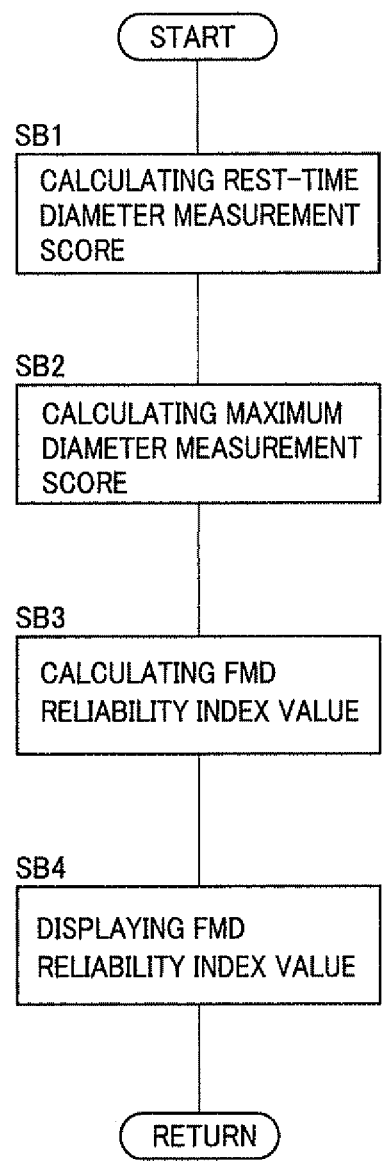
FIG. 16 is a flow chart illustrating a major control function of the electronic control device of FIG. 8 which is different from that of FIG. 15, namely, a control operation to calculate index values indicative of the accuracy of measurements for FMD evaluation.

FIG. 16 is the flow chart illustrating a major control function of the blood vessel inspecting apparatus 22 (electronic control device 28), which is different from that of FIG. 15, namely, a control operation to calculate the index values indicative of the accuracy of measurements for FMD evaluation. This control operation illustrated in FIG. 16 may be performed alone, or concurrently with other control operation or operations.

Initially, SB1 corresponding to the index value calculating means 84 and reflected wave recognition control means 86 is implemented to effect the above-described reflected wave recognition control for each of the front wall portion $BR_F$ and back wall portion $BR_B$, and for each of the plurality of reflected wave signals $SG_{EC}$ which are used to obtain the above-described longitudinal cross sectional blood vessel image for measuring the rest-time diameter $d_a$ for FMD evaluation before the blood vessel releasing from the blood flow obstruction. Described in detail, the above-described reflected wave recognition control is not implemented for all of the plurality of reflected wave signals $SG_{EC}$, but implemented for each of the plurality of reflected wave signals $SG_{EC}$ received within the above-described observation range AOB. On the basis of a result of this reflected wave recognition control, the front wall portion image clarity index value $XCR_F$ and the back wall portion image clarity index value $XCR_B$ upon measurement of the above-described rest-time diameter $d_a$ are calculated, and an average of these calculated index values is calculated as the above-described rest-time diameter measurement score XCR1.

In SB2 corresponding to the index value calculating means 84 and the reflected wave recognition control means 86, the above-described reflected wave recognition control is effected for each of the front wall portion $BR_F$ and back wall portion $BR_B$, and for each of the plurality of reflected wave signals $SG_{EC}$ which are used to obtain the above-described longitudinal cross sectional blood vessel image for measuring the maximum diameter $d_{MAX}$ for FMD evaluation after the blood vessel releasing from the blood flow obstruction. Described in detail, the above-described reflected wave recognition control is not implemented for all of the plurality of reflected wave signals $SG_{EC}$, but implemented for each of the plurality of reflected wave signals $SG_{EC}$ received within the above-described observation range AOB, as in the above-described SB1. On the basis of a result of this reflected wave recognition control, the front wall portion image clarity index value $XCR_F$ and the back wall portion image clarity index value $XCR_B$ upon measurement of the above-described maximum diameter $d_{MAX}$ are calculated, and an average of these calculated index values is calculated as the above-described maximum diameter measurement score XCR2.

In SB3 corresponding to the index value calculating means 84, the FMD reliability index value $XCR_{FMD}$ is calculated on the basis of the above-described rest-time diameter measurement score XCR1 and maximum diameter measurement score XCR2 and according to the above-indicated Equation (3).

In SB4 corresponding to the display control means 90, the above-described FMD reliability index value $XCR_{FMR}$ is displayed on the monitoring image display device 30, together with a result of the FMD evaluation, for instance, together with the above-described blood vessel dilatation ratio evaluating value (% FMD value) $R_{MAX}$.

The present embodiment has the following advantages (A1) through (A8):

(A1) The present embodiment is configured such that the cross sectional blood vessel image generating means (longitudinal cross sectional blood vessel image generating means) 82 successively generates the longitudinal cross sectional image of the blood vessel 20 located below the skin of the live body 14 based on the reflected wave signal $SG_{EC}$ of the ultrasonic obtained, by using the ultrasonic probe 24 placed on the skin of the live body 14, and the index value calculating means 84 calculates the index values indicative of the degree of clarity of the image of the intima-media complex IMC existing within the longitudinal cross sectional image of the blood vessel 20 generated by the cross sectional blood vessel image generating means 82. Accordingly, the operator of the blood vessel inspecting apparatus 22 is not required to determine the degree of clarity of the image directly from the longitudinal cross sectional image of the above-described blood vessel 20 (longitudinal cross sectional blood vessel image), but can objectively determine the degree of clarity of the image from the index values of clarity of the image representing the intima-media complex IMC of the above-described blood vessel 20, so that the operator can easily make a fine positional adjustment of the ultrasonic probe 24 so as to further improve the index values, whereby the longitudinal cross sectional blood vessel image can be efficiently obtained with a high degree of clarity, even where the operator's manipulation skill is low.

(A2) The present embodiment is further configured such that the above-described index value calculating means 84 calculates the front wall portion image clarity index value $XCR_F$ indicative of the degree of clarity of the image of the intima-media complex IMC of the front wall portion $BR_F$ within the above-described longitudinal cross sectional blood vessel image, and the back wall portion image clarity index value $XCR_B$ indicative of the degree of clarity of the image of the intima-media complex IMC of the back wall portion $BR_F$ within the above-described longitudinal cross sectional blood vessel image. Accordingly, the operator, for example, can efficiently position the ultrasonic probe 24 so as to further increase the degrees of clarity of the images of the front wall portion $BR_F$ and back wall portion $BR_F$ within the above-described longitudinal cross sectional blood vessel image, on the basis of the front wall portion image clarity index value $XCR_F$ and the back wall portion image clarity index value $XCR_B$.

(A3) The present embodiment is further configured such that the reflected wave recognition control means 86 configured to implement the reflected wave recognition control for each of the plurality of reflected wave signals $SG_{EC}$ received by the long-axis ultrasonic detector array 24c at the mutually different positions of reception in the longitudinal direction of the blood vessel, and for each of the above-described front wall portion $BR_F$ and the above-described back wall portion $BR_B$, to detect according to the relationship as indicated in FIG. 10 between the amplitude $AM_{SG}$ of each reflected wave signal $SG_{EC}$ and the position $PT_R$ in the diametric direction of the blood vessel 20: the first peak PK1 of each reflected wave signal $SG_{EC}$ at which the amplitude $AM_{SG}$ is larger than the predetermined first peak determining threshold value $LT1_{PK}$; the bottom BTM of each reflected wave signal $SG_{EC}$ which is generated at the position of the blood vessel 20 located outwardly of the position of generation of the first peak PK1 in the diametric direction of the blood vessel 20 and at which the amplitude $AM_{SG}$ is smaller than the predetermined bottom determining threshold value $LT_{BTM}$; and the second peak PK2 of each reflected wave signal $SG_{EC}$ which is generated at the position of the blood vessel 20 located outwardly of the position of generation of the first peak PK1 in the diametric direction of the blood vessel 20 but located within the spacing distance from the position of generation of the first peak PK1 not exceeding the predetermined peak-to-peak distance threshold value $LT_{SP}$, with the bottom BTM being located therebetween, and at which the amplitude $AM_{SG}$ is larger than the predetermined second peak determining threshold value $LT2_{PK}$. Further, the index value calculating means 84 calculates the above-described front wall portion image clarity index value $XCR_F$ on the basis of the number $QL_{SG}$ of the reflected wave signals $SG_{EC}$ all of the above-described first peak PK1, the above-described bottom BTM and the above-described second peak PK2 of which have been detected by the above-described reflected wave recognition control implemented by the reflected wave recognition control means 86 for the front wall portion $BR_F$, and the back wall portion image clarity index value $XCR_B$ on the basis of the number $QL_{SG}$ of the reflected wave signals $SG_{EC}$ all of the above-described first peak PK1, the above-described bottom BTM and the above-described second peak PK2 of which have been detected by the above-described reflected wave recognition control implemented by the reflected wave recognition control means 86 for the back wall portion $BR_B$. Accordingly, the front wall portion image clarity index value $XCR_F$ and the back wall portion image clarity index value $XCR_B$ are calculated on the basis of non-fluctuating parameters, so that the above-described front wall portion image clarity index values $XCR_F$ and the above-described back wall portion image clarity index values $XCR_B$ which are calculated upon different blood vessel inspections can be compared with each other.

(A4) The present embodiment is further configured such that the reflected wave recognition control means 86 implements the above-described reflected wave recognition control for those of the above-described reflected wave signals $SG_{EC}$ which are received within the predetermined observation range AOB in the longitudinal direction of the blood vessel 20. Accordingly, it is possible to reduce a control load in the calculation of the above-described front wall portion image clarity index value $XCR_F$ and the above-described back wall portion image clarity index value $XCR_B$, as compared where the above-described reflected wave recognition control is implemented for all of the plurality of the above-described reflected wave signals $SG_{EC}$ received by the long-axis ultrasonic detector array 24c to generate the above-described longitudinal cross sectional blood vessel image.

(A5) The present embodiment is further configured to implement the above-described reflected wave recognition control such that the amplitude $AM_{SG}$ of each reflected wave signal $SG_{EC}$ is compared with the above-described first peak determining threshold value $LT1_{PK}$, the above-described bottom determining threshold value $LT_{BTM}$, and the second peak determining threshold value $LT2_{PK}$, so that the above-described first peak PK1, the above-described bottom BTM and the above-described second peak PK2 can be easily detected from the reflected wave signal $SG_{EC}$. It is noted here that the amplitude $AM_{SG}$ of each reflected wave signal $SG_{EC}$ may be replaced by a brightness value obtained by conversion of the amplitude. In this case, the brightness value is compared with the above-described first peak determining threshold value $LT1_{PK}$, the above-described bottom determining threshold value $LT_{BTM}$, and the second peak determining threshold value $LT2_{PK}$.

(A6) The present embodiment is further configured such that the ultrasonic probe 24 is provided with the pair of parallel ultrasonic detector arrays consisting of the first short-axis ultrasonic detector array 24a and the second short-axis ultrasonic detector array 24b each of which has the plurality of ultrasonic oscillators arranged linearly in the direction perpendicular to the longitudinal direction of the blood vessel 20, and the long-axis ultrasonic detector array 24c which is disposed adjacent to the intermediate portion of the first short-axis ultrasonic detector array 24a and the second short-axis ultrasonic detector array 24b and which has the plurality of ultrasonic oscillators linearly arranged in the longitudinal direction of the blood vessel 20, the first and second short-axis ultrasonic detector arrays 24a, 24b and the long-axis ultrasonic detector array 24c lying in one plane, as shown in FIG. 2. The longitudinal cross sectional blood vessel image generating means 82 generates the above-described longitudinal cross sectional blood vessel image, on the basis of the reflected wave signals $SG_{EC}$ of the ultrasonic wave received by the long-axis ultrasonic detector array 24c. Accordingly, the above-described longitudinal cross sectional blood vessel image can be generated by using the ultrasonic wave probe which is practically available.

(A7) The present embodiment is further configured such that the blood vessel diameter measuring means 88 measures in advance the rest-time diameter $d_a$ of the blood vessel 20 before releasing of the blood vessel 20 from blood flow obstruction, the maximum diameter $d_{MAX}$ of the blood vessel 20 after the releasing of the blood vessel 20 from the blood flow obstruction, and the maximum value $R_{MAX}$ of the diameter change ratio of the blood vessel 20 after the releasing of the blood vessel 20 from the blood flow obstruction, with respect to the rest-time diameter $d_a$ of the blood vessel 20, and the index value calculating means 84 calculates the index value (FMD reliability index value) $XCR_{FMD}$ indicative of the degree of reliability of the maximum diameter change ratio value $R_{MAX}$ of the blood vessel 20 measured by the blood vessel diameter measuring means 88 after the releasing of the blood vessel 20 with respect to the rest-time diameter $d_a$ of the blood vessel 20, on the basis of the front wall portion image clarity index value $XCR_F$ and the back wall portion image clarity index value $XCR_B$ upon measurement of the above-described rest-time diameter $d_a$, and the front wall portion image clarity index value $XCR_F$ and the back wall portion image clarity index value $XCR_B$ upon measurement of the above-described maximum diameter dr x. Where a plurality of maximum values $R_{MAX}$ of the diameter change ratio after the blood vessel releasing from the blood flow obstruction with respect to the rest-time diameter $d_a$ of the blood vessel 20 are measured and compared with each other, the above-described FMD reliability index value $XCR_{FMD}$, each obtained for each maximum value $R_{MAX}$, can be used to eliminate those of the plurality of maximum values $R_{MAX}$ the accuracy of measurement of which is low, so that the reliability of a result of FMD evaluation, for instance, can be further improved. Further, it is possible to make an objective clinic judgment as to whether a re-inspection is necessary when the FMD reliability index value $XCR_{FMD}$ is low. The FMD reliability index value $XCR_{FMD}$ can be a yardstick to evaluate a degree of progress objectively when an operator practice to measure a blood vessel lumen diameter $d_1$ in FMD evaluation method.

(A8) The present embodiment is further configured such that, as sown in FIG. 14, the above-described index value calculating means 84 commands the monitoring image display device 30 to display the above-described front wall portion image clarity index value $XCR_F$ and the above-described back wall portion image clarity index value $XCR_B$, not only as numerical values, but also as two images or two graphic figures (two sectors) which are continuously variable according to the index values $XCR_F$, $XCR_B$ and which are comparable with each other. Accordingly, the operator can intuitively perceive the degrees of clarity of the images of the front wall portion $BR_F$ and the back wall portion, and more efficiently improve the clarity of the images, than where the degrees of clarity of the images are indicated by only the numerical values of $XCR_F$, $XCR_B$.

Another embodiment of this invention will be described next. In the following description, the same reference signs will be used to identify the same elements of the embodiments, the description of which is omitted.

Embodiment 2

In the first embodiment described above, the above-described front wall portion image clarity index value $XCR_F$ and back wall portion image clarity index value $XCR_B$ are calculated and displayed for the operator of the blood vessel inspecting apparatus 22 to make the manual fine positional adjustment of the ultrasonic probe 24 placed on the skin of the live body 14. However, the fine positional adjustment of the ultrasonic probe 24 may be automatically made by the multi-axes drive device 26 on the basis of the front wall portion image clarity index value $XCR_F$ and back wall portion image clarity index value $XCR_B$, so that the degree of clarity of the intima-media complex IMC within the above-described longitudinal cross sectional blood vessel image is not lower than a predetermined lower limit. The present second embodiment described below is configured to perform a control operation for the automatic fine positional adjustment of the ultrasonic probe 24. This control operation may replace the above-described display control according to the first embodiment, or may be performed concurrently with the display control of the first embodiment described above. Aspects of the second embodiment which are different from those of the first embodiment will be primarily described, without redundant description of the common aspects of the first and second embodiments.

Figure 17:
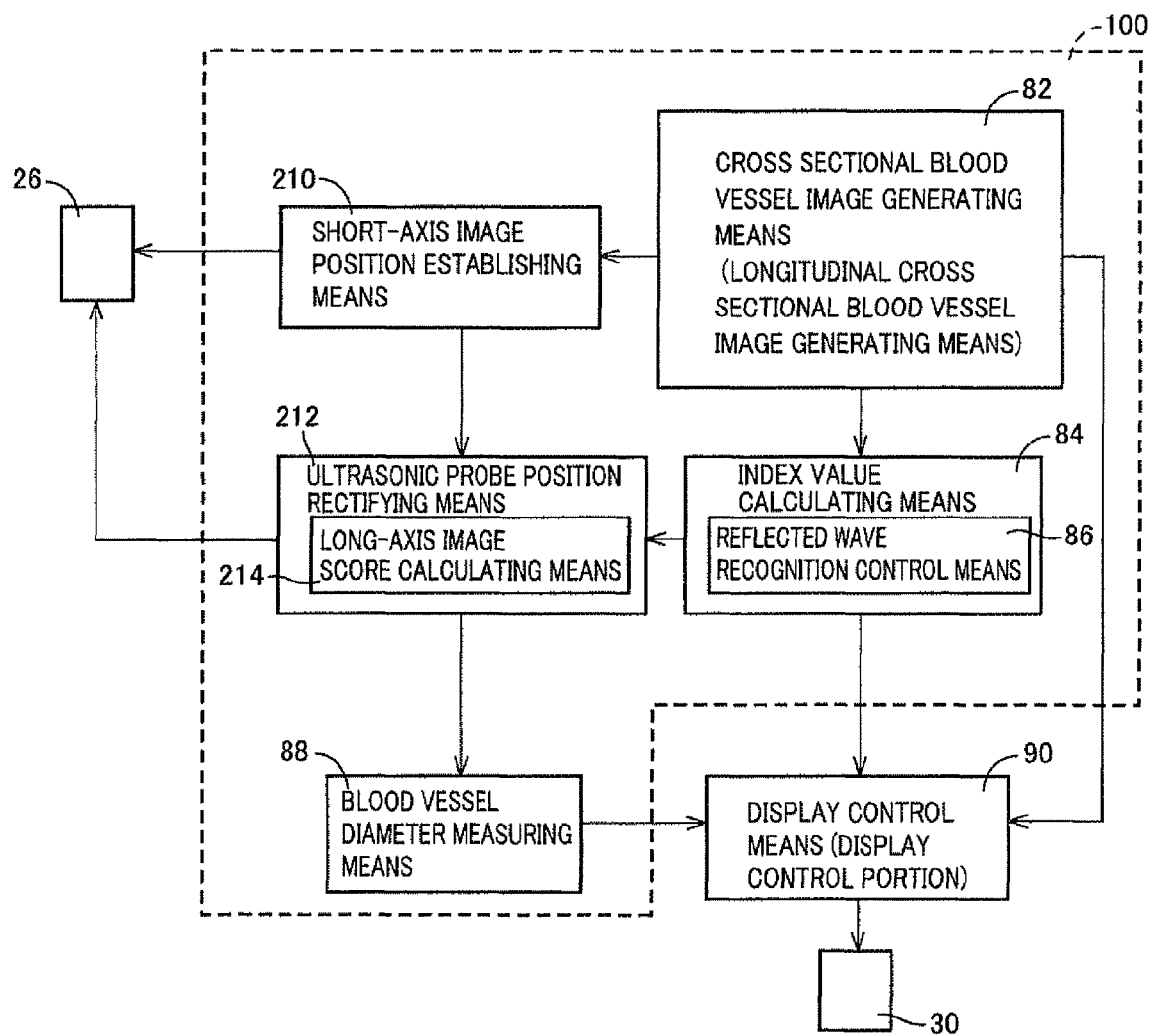
FIG. 17 is a functional block diagram corresponding to that of FIG. 8, for explaining major control functions of an electronic control device included in the ultrasonic blood vessel inspecting apparatus of FIG. 1 according to a second embodiment of this invention.

FIG. 17 is the functional block diagram corresponding to that of FIG. 8 according to the first embodiment, for explaining major control functions of the blood vessel inspecting apparatus 22 (blood vessel image evaluating portion 100). The blood vessel image evaluating portion 100 according to the present embodiment is provided with the cross sectional blood vessel image generating means 82 the index value calculating means 84 and the blood vessel diameter measuring means 88, as in the first embodiment, and is further provided with a short-axis image position determining portion in the form of short-axis image position establishing means 210, and an ultrasonic probe position rectifying portion in the form of ultrasonic probe position rectifying means 212. The ultrasonic probe position rectifying means 212 is provided with a long-axis image score calculating portion in the form of long-axis image score calculating means 214.

The cross sectional blood vessel image generating means 82 is configured to successively generate: the transverse cross sectional image of the blood vessel 20, namely, the first transverse cross sectional blood vessel image to be displayed in the first short-axis image display region G1, on the basis of the reflected wave signals $SG_{EC}$ of the ultrasonic wave received by the first short-axis ultrasonic detector array 24a; the transverse cross sectional image of the blood vessel 20, namely, the second transverse cross sectional blood vessel image to be displayed in the second short-axis image display region G2, on the basis of the reflected wave signals $SG_{EC}$ of the ultrasonic wave received by the second short-axis ultrasonic detector array 24b; and the longitudinal cross sectional image of the blood vessel 20, namely, the longitudinal cross sectional blood vessel image to be displayed in the long-axis image display region G3, on the basis of the reflected wave signals $SC_{EC}$ of the ultrasonic received by the long-axis ultrasonic detector array 24c, as in the first embodiment.

The short-axis image position establishing means 210 is configured to recognize a center position $CR_{BV}$ of the blood vessel 20 (blood vessel transverse cross section center $CR_{BV}$) in each of the above-described first transverse cross sectional blood vessel image and the above-described second transverse cross sectional blood vessel image which are generated by the cross sectional blood vessel image generating means 82. Then, the short-axis image position establishing means 210 operates the multi-axes drive device 26 to position the ultrasonic probe 24 such that a distance between the first short-axis ultrasonic detector array 24a and the center of the blood vessel 20 (blood vessel cross section center $CR_{BV}$) is equal to a distance between the second short-axis ultrasonic detector array 24b and the center of the blood vessel 20 (blood vessel cross section center $CR_{BV}$), and such that the image of the blood vessel 20 is located at a widthwise central portion of each of the first and second short-axis image display regions G1 and G2. Described by reference to FIG. 4, the multi-axes drive device 26 is operated to position the ultrasonic probe 24 such that a=b, c=d, and e=f, namely, such that the ultrasonic probe 24 is located at the above-described predetermined measuring position PT1. For instance, a relationship between a displacement (amount and direction of the displacement) of the blood vessel center position $CR_{BV}$ with respect to the above-described predetermined measuring position PT1 in each of the above-described first and second transverse cross sectional blood vessel images, and an amount of operation of each actuator of the multi-axes drive device 26 required to locate the ultrasonic probe 24 at the above-described predetermined measuring position PT1 is obtained by experimentation in advance, and is preset in the short-axis image position establishing means 210. After the short-axis image position establishing means 210 has recognized the blood vessel center position $CR_{BV}$ in each of the above-described first and second transverse cross sectional blood vessel images, the short-axis image position establishing means 210 calculates the displacement (amount and direction of the displacement) of the blood vessel center position $CR_{BV}$ with respect to the above-described predetermined measuring position PT1 Then, the short-axis image position establishing means 210 determines whether the calculated displacement of the blood vessel center position $CR_{BV}$ is zero or within a predetermined permissible range in which the displacement can be considered substantially zero. If it is determined that the displacement of the blood vessel center position $CR_{BV}$ is not zero or within the above-described predetermined permissible range, the short-axis image position establishing means 210 determines the amount of operation of each actuator of the multi-axes drive device 26, on the basis of the calculated displacement of the blood vessel center position $CR_{BV}$ and according to the preset relationship between the displacement of the blood vessel center position $CR_{BV}$ and the amount of operation of each actuator. The short-axis image position establishing means 210 repeats the recognition of the blood vessel center position $CR_{BV}$, the calculation of the displacement of the blood vessel center position $CR_{BV}$ with respect to the above-described predetermined measuring position PT1, and the control operation of the multi-axes drive device 26, until the displacement of the above-described blood vessel center position $CR_{BV}$ is zeroed or falls within the above-described predetermined permissible range, for instance, each time the cross sectional blood vessel image generating means 82 generates the first and second transverse cross sectional blood vessel images. If it is determined that the displacement of the blood vessel center position $CR_{BV}$ is zero or falls within the above-described predetermined permissible range, the short-axis image position establishing means 210 terminates the control operation of the multi-axes drive device 26, and informs the ultrasonic probe position rectifying means 212 that the positioning of the ultrasonic probe 24 on the basis of the transverse cross sectional blood vessel images is completed.

The long-axis image score calculating means 214 is configured to calculate a value $BR_{FB}$ indicative of the overall degree of clarity of the image of the intima-media complex IMC at both of the front wall portion $BR_F$ and back wall portion $BR_B$ within the longitudinal cross sectional blood vessel image, namely, an overall clarity index value $BR_{FB}$, on the basis of the front wall portion image clarity index value $XCR_F$ and back wall portion image clarity index value $XCR_B$, each calculated by the index value calculating means 84. While the overall clarity index value $BR_{FB}$ may be an average or a sum of the front wall portion image clarity index value $XCR_F$ and back wall portion image clarity index value $XCR_B$, the overall clarity index value $BR_{FB}$ is the average of the index values $XCR_F$ and $XCR_B$, that is, an index value average. The long-axis image score calculating means 214 calculates the above-described overall clarity index value $BR_{FB}$ each time the index value calculating means 84 calculates the front wall portion image clarity index value $XCR_F$ and the back wall portion image clarity index value $XCR_B$, in other words, each time the cross sectional blood vessel image generating means 82 receives (obtains) the reflected wave signals $SG_{EC}$ of the ultrasonic wave for generating the longitudinal cross sectional blood vessel image.

The ultrasonic probe position rectifying means 212 is configured to operate the multi-axes drive device 26 to position the ultrasonic probe 24 after completion of positioning of the ultrasonic probe 24 under the control of the short-axis image position establishing means 210, such that the value (overall clarity index value $BR_{FB}$) calculated on the basis of the front wall portion image clarity index value $XCR_F$ and the back wall portion image clarity index value $XCR_B$, is equal to or larger than a predetermined threshold value (index value average threshold value) $LBR1_{FB}$. That is, the ultrasonic probe position rectifying means 212 makes a fine positional adjustment of the ultrasonic probe 24. For instance, the above-described index value average threshold value $LBR1_{FB}$ is predetermined by experimentation such that the intima-media complex IMC within the longitudinal cross sectional blood vessel image is clear enough to permit measurement of the blood vessel diameter. Described more specifically, the ultrasonic probe position rectifying means 212 determines whether the overall clarity index value $BRF_B$ calculated by the long-axis image score calculating means 214 is equal to or larger than the above-described index value average threshold value $LBR1_{FB}$, and operates the multi-axes drive device 26 to displace the ultrasonic probe 24 by a predetermined small distance in a direction for increasing the overall clarity index value $BR_{FB}$, if it is determined that the overall clarity index value $BR_{FB}$ is not equal to or larger than the index value average threshold value $LBR1_{FB}$. The ultrasonic probe position rectifying means 212 repeats this displacement of the ultrasonic probe 24 by the predetermined small distance until the overall clarity index value $BR_{FB}$ has become equal to or larger than the index value average threshold value $LBR1_{FB}$. When it is determined that the overall clarity index value $BR_{FB}$ has become equal to or larger than the index value average threshold value $LBR1_{FB}$, the ultrasonic probe position rectifying means 212 terminates the control operation of the multi-axes drive device 26, and informs the blood vessel diameter measuring means 88 that the fine positional adjustment of the ultrasonic probe 24 is completed. If it is found in the next cycle that the overall clarity index value $BR_{FB}$ decreases after the movement of the ultrasonic probe 24 by the above-described predetermined small distance by operation of the multi-axes drive device 26, the ultrasonic probe position rectifying means 212 then operates the multi-axes drive device 26 to move the ultrasonic probe 24 back to the original position and to further move the ultrasonic probe 24 by the above-described predetermined small distance in the direction opposite to the direction of the prior movement for minute position adjustment of the ultrasonic probe 24. It is also noted that a range of the overall clarity index value $BR_{FB}$ equal to or higher than the index value average threshold value $LBR1_{FB}$ is a predetermined target range according to the present invention.

The blood vessel diameter measuring means 88 has, in addition to the function described above with respect to the first embodiment, a function of initiating the FMD measurement, more specifically, the measurement of the blood vessel lumen diameter $d_1$ ($d_a$, $d_{MAX}$), when the blood vessel diameter measuring means 88 is informed by the ultrasonic probe position rectifying means 212 that the fine positional adjustment of the ultrasonic probe 24 is completed.

Figure 18:
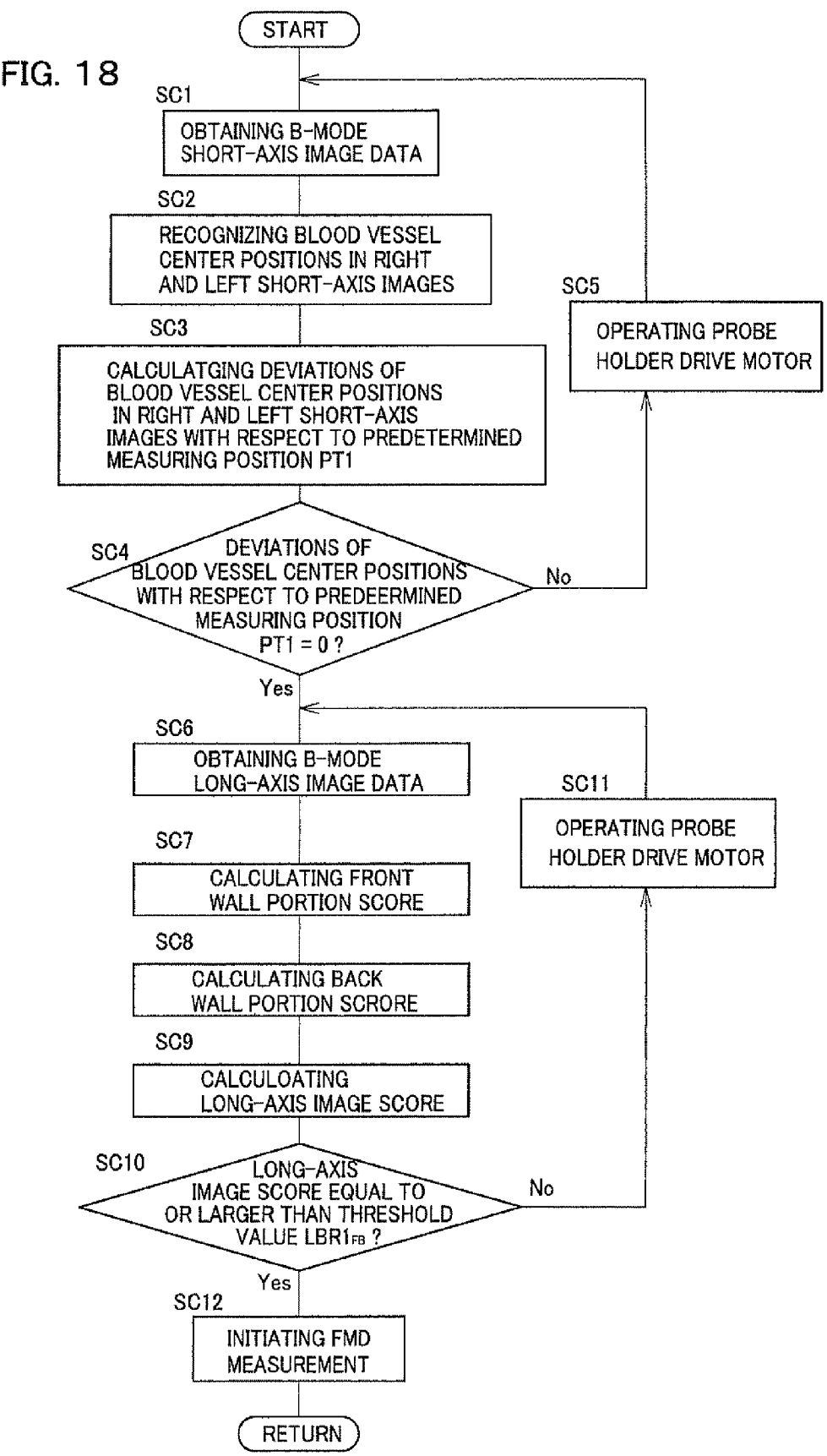
FIG. 18 is a flow chart corresponding to that of FIG. 15, illustrating a major control operation of the electronic control device of FIG. 17, namely, a control operation to automatically locate the ultrasonic probe at an FMD measurement position according to the second embodiment.

FIG. 18 is the flow chart corresponding to that of FIG. 15 according to the first embodiment, illustrating a major control operation of the blood vessel inspecting apparatus 22 (electronic control device 28) according to the present embodiment, namely, a control operation to automatically locate the ultrasonic probe 24 at an FMD measurement position. SC6, SC7 and SC8 in FIG. 18 which are respectively identical with the SA2, SA3 and SA4 in FIG. 15 will not be described. The control operation illustrated in FIG. 18 may be performed alone or concurrently with other control operation or operations.

In SC1 corresponding to the cross sectional blood vessel image generating means 82, the B-mode short-axis image data are obtained. That is, the first short-axis ultrasonic detector array 24*a* scans and receives (obtains) the reflected wave signals $SG_{EC}$ of the ultrasonic wave at the predetermined reflected wave reception time interval $PC_{RV}$ in the longitudinal direction of the detector array 24*a*, while the second short-axis ultrasonic detector array 24*b* scans and receives (obtains) the reflected wave signals $SG_{EC}$ of the ultrasonic wave at the predetermined reflected wave reception time interval $PC_{RV}$ in the longitudinal direction of the detector array 24*b*. The B-mode short-axis image data (reflected wave signals $SG_{EC}$) obtained as described above are stored in the memory device of the electronic control device 28. The above-described first transverse cross sectional blood vessel image is generated on the basis of the reflected wave signals $SG_{EC}$ of the ultrasonic wave received by the first short-axis ultrasonic detector array 24*a*, while the above-described second transverse cross sectional blood vessel image is generated on the basis of the reflected wave signals $SG_{EC}$ of the ultrasonic wave received by the second short-axis ultrasonic detector array 24*b*.

In SC2 corresponding to the short-axis image position establishing means 210, the center position $CR_{BV}$ of the blood vessel 20 is recognized in each of the right and left short-axis images on the monitoring image display device 30, namely, in each of the above-described first transverse cross sectional blood vessel image and the above-described second transverse cross sectional blood vessel image.

In SC3 corresponding to the short-axis image position establishing means 210, the displacement (amount and direction of the displacement) of the blood vessel center position $CR_{BV}$ in each of the above-described first and second transverse cross sectional blood vessel images with respect to the above-described predetermined measuring position PT1 is calculated.

SC4 corresponding to the short-axis image position establishing means 210 is implemented to determine whether the displacement of the blood vessel center position CRBV calculated in the above-described SC3 is zero or substantially zero. If an affirmative determination is obtained in this SC4, that is, if the displacement of the above-described blood vessel center position CRBV is zero or substantially zero, the control flow goes to SC6 to obtain the above-decribed B-mode long-axis image data with the long-axis ultrasonic detector array 24c. If a negative determination is obtained in this SC4, on the other hand, the control flow goes to SC5.

In SC5 corresponding to the short-axis image position establishing means 210, each actuator of the multi-axes drive device 26, that is, a probe holder motor is operated to reduce the displacement of the above-described blood vessel center position $CR_{BV}$. For instance, the multi-axes drive device 26 is operated in the direction to reduce the displacement of the above-described blood vessel center position $CR_{BV}$, on the basis of the displacement and according to the relationship obtained in advance by experimentation. SC5 is followed by SC1.

In SC9 following SC8, the average of the front wall portion image clarity index value (front wall portion score) $XCR_F$ calculated in SC7 and the back wall portion image clarity index value (back wall portion score) $XCR_B$ calculated in SC8 is calculated, and the calculated average is determined as the above-described overall clarity index value $BR_{FB}$, namely, as a score of the above-described longitudinal cross sectional blood vessel image (long-axis image). This SC9 corresponds to the long-axis image score calculating means 214.

SC10 corresponding to the ultrasonic probe position rectifying means 212 is implemented to determine whether the overall clarity index value $BR_{FB}$ calculated in the above-described SC9 is equal to or larger than the above-described index value average threshold value $LBR1_{FB}$. If an affirmative determination is obtained in this SC10, that is if the above-described overall clarity index value $BR_{FB}$ calculated in the above-described SC9 is equal to or larger than the above-described index value average threshold value $LBR1_{FB}$, the control flow goes to SC12. If a negative determination is obtained in this SC10, the control flow goes to SC11.

In SC11 corresponding to the ultrasonic probe position rectifying means 212, each actuator (probe holder motor) of the multi-axes drive device 26 is operated in the direction to increase the above-described overall clarity index value $BR_{FB}$. For example, the position of the ultrasonic probe 24 is moved by the above-described predetermined small distance by an operation of the multi-axes drive device 26. If it is found in the next cycle that the overall clarity index value $BR_{FB}$ decreases after the movement of the ultrasonic probe 24 by the above-described predetermined small distance by the multi-axes drive device 26, the ultrasonic probe position rectifying means 212 then operates the multi-axes drive device 26 to move the ultrasonic probe 24 to the original position and to further move the ultrasonic probe 24 by the above-described predetermined small distance in the direction opposite to the direction of the prior movement. SC11 is followed by SC6.

In SC12 corresponding to the blood vessel diameter measuring means 88, the FMD measurement, more specifically, the measurement of the blood vessel lumen diameter $d_1$ ($d_a$, $d_{MAX}$) is initiated.

The present embodiment has the following advantages, in addition to the advantages of the first embodiment described above. In the present embodiment, the short-axis image position establishing means 210 operates the multi-axes drive device 26 to position the ultrasonic probe 24 such that the distance between the first short-axis ultrasonic detector array 24a and the center of the blood vessel 20 (blood vessel transverse cross section center $CR_{BV}$) is equal to the distance between the second short-axis ultrasonic detector array 24b and the center of the blood vessel 20 (blood vessel transverse cross section center $CR_{BV}$), and such that the image of the blood vessel 20 is located at the widthwise central portion of each of the first and second short-axis image display regions G1 and G2 in monitoring image display device 30. Then, the ultrasonic probe position rectifying means 212 operates the multi-axes drive device 26 to position the ultrasonic probe 24 after completion of positioning of the ultrasonic probe 24 under the control of the short-axis image position establishing means 210, such that the value (overall clarity index value $BR_{FB}$) calculated on the basis of the front wall portion image clarity index value $XCR_F$ and the back wall portion image clarity index value $XCR_B$ is equal to or larger than the predetermined index value average threshold value $LBR1_{FB}$. Accordingly, an operator's load of manipulation can be reduced. Further, the longitudinal cross sectional blood vessel image can be made clearer even where the operator's manipulation skill is considerably low, as compared with the image when the operator makes the manual fine positional adjustment of the ultrasonic probe 24 so as to increase the front wall portion image clarity index value $XCR_F$ and the back wall portion image clarity index value $XCR_B$. In addition, the FMD measurement including the fine positional adjustment of the ultrasonic probe 24 to improve the clarity of the longitudinal cross sectional blood vessel image is achieved.

While the embodiments of the present invention have been described in detail by reference to the drawings, for illustrative purpose only, it is to be understood that the invention may be embodied with various changes and improvements which may occur to those skilled in the art.

For example, the above-indicated Equation (1) used to calculate the above-described front wall portion image clarity index value $XCR_F$ and the above-indicated Equation (2) used to calculate the above-described back wall portion image clarity index value $XCR_B$ in the illustrated embodiments may be replaced by other methods of calculation.

Figure 19:
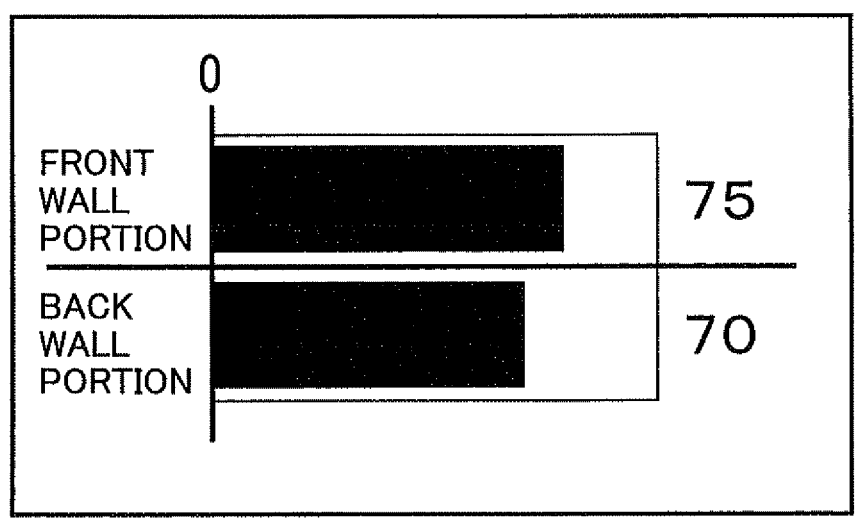
FIG. 19 is a view corresponding to that of FIG. 14, indicating a front wall portion image clarity index value and a back wall portion image clarity index value which are displayed on the monitoring image display device in a display pattern different from that of FIG. 14.

In the illustrated embodiments, each of the above-described front wall portion image clarity index value $XCR_F$ and back wall portion image clarity index value $XCR_B$ is displayed in the form of a sector on the monitoring image display device 30, as indicated in FIG. 14. However, those image clarity index values may be displayed in any other form such as bars as indicated in FIG. 19 by way of example. While each of the above-described front wall portion image clarity index value $XCR_F$ and back wall portion image clarity index value $XCR_B$ is displayed in the form of the graphic figures (sectors) as well as numerical values in the illustrated embodiments on the monitoring image display device 30, only the numerical values or only the graphic figures may be displayed.

In the illustrated embodiments, each of the above-described front wall portion image clarity index value $XCR_F$ and back wall portion image clarity index value $XCR_B$ is displayed on the monitoring image display device 30 used to display the above-described longitudinal cross sectional blood vessel image and the above-described transverse cross sectional blood vessel images, as indicated in FIG. 13. However, those clarity index values may be displayed on another display device independent of the monitoring image display device 30.

In the illustrated embodiments, the above-described FMD reliability index value $XCR_{FMD}$ is calculated by averaging according to the above-indicated Equation (3), the average of the front wall portion image clarity index value $XCR_F$ and back wall portion image clarity index value $XCR_B$ upon measurement of the above-described rest-time diameter $d_a$, and the average of the front wall portion image clarity index value $XCR_F$ and back wall portion image clarity index value $XCR_B$ upon measurement of the above-described maximum diameter $d_{MAX}$. However, the method of calculation of the FMD reliability index value $XCR_{FMD}$ is not limited to this specific method. For instance, the FMD reliability index value $XCR_{FMD}$ may be calculated by summing all of those index values $XCR_F$ and $XCR_B$.

The reflected wave recognition control means 86 in the illustrated embodiments is configured to implement the above-described reflected wave recognition control with respect to the reflected wave signals $SG_{EC}$ as indicated in FIG. 10. However, the reflected wave signals $SG_{EC}$ may be subjected to a sharpening process prior to the reflected wave recognition control, by using a sharpening (clarifying) filter well known in the art, for sharpening and clarifying the peaks and bottoms of the reflected wave signals $SG_{EC}$. This sharpening process may be an unsharp masking process or a selective image clarifying process well known in the art. The unsharp masking process is a method of clarifying a blurred image by removing its secondary differential image (Laplacian image), and the selective image clarifying process is a method of selectively clarifying edge portions of an image by extracting only the Laplacian image components of the edge portions to reduce an influence of noises.

While the illustrated embodiments are arranged to implement the FMD measurement after the positioning of the ultrasonic probe 24, the principle of the present invention is equally advantageously applicable to a control device configured to implement IMT (intima-media thickness) inspection, or ultrasonic observation of the carotid artery.

In the illustrated embodiments, the front wall portion image clarity index value $XCR_F$ and back wall portion image clarity index value $XCR_B$ are calculated on the basis of the result of the above-described reflected wave recognition control. However, these clarity index values may be calculated in any other manner, provided the clarity index values are calculated in relation to the degree of clarity of the intima-media complex IMC within the above-described longitudinal cross sectional blood vessel image.

Although the electronic control device 28 is provided with the blood vessel diameter measuring means 88 in the illustrated embodiments, the electronic control device 28 may not be provided with the blood vessel diameter measuring means 88.

It is noted that the brachium 16 shown in FIG. 1 in the illustrated embodiments is an upper arm of a human body.

It is to be understood that the illustrated embodiments described above may be combined together, with specific features given priority of selection.

It is to be understood that the present invention may be embodied with various other changes not illustrated herein, without departing from the spirit of this invention.

NOMENCLATURE OF REFERENCE SIGNS

14: Live body
20: Blood vessel
22: Blood vessel inspecting apparatus (Ultrasonic blood vessel inspecting apparatus)
24: Ultrasonic probe
24a: First short-axis ultrasonic detector array
24b: Second short-axis ultrasonic detector array
24c: Long-axis ultrasonic detector array
26: Multi-axes drive device
30: Monitoring image display device (Image display device)
82: Cross sectional blood vessel image generating means (Longitudinal cross sectional blood vessel image generating means)
84: Index value calculating means
86: Reflected wave recognition control means
88: Blood vessel diameter measuring means
210: Short-axis image position establishing means
212: Ultrasonic probe position rectifying means
IMC: Intima-media complex
$BR_F$: Front wall portion
$BR_B$: Back wall portion
$SG_{EC}$: Reflected wave signal

The invention claimed is:

1. An ultrasonic blood vessel inspecting apparatus comprising:
    an ultrasonic probe configured to be placed on skin of a live body, irradiate an ultrasonic wave toward a blood vessel, and receive reflected wave signals of the ultrasonic wave; and
    a processor having a program stored therein for causing the processor to perform executable portions,
    wherein the executable portions comprise:
        a longitudinal cross sectional blood vessel image generating portion configured to generate a longitudinal cross sectional image of the blood vessel located below the skin of the live body, based on the reflected wave signals of the ultrasonic wave by using the ultrasonic probe,
        an index value calculating portion configured to calculate an intima-media complex image clarity index value indicative of a degree of clarity of an image which represents an intima-media complex of said blood vessel and which exists within said longitudinal cross sectional image of the blood vessel, wherein said index value calculating portion calculates a front wall portion image clarity index value indicative of the degree of clarity of an image of a front wall portion of said intima-media complex within said longitudinal cross sectional image of the blood vessel, and a back wall portion image clarity index value indicative of the degree of clarity of an image of a back wall portion of said intima-media complex within said longitudinal cross sectional image of the blood vessel, said front wall portion being one of opposite wall portions of the blood vessel on the side of said ultrasonic probe while said back wall portion being the other of the opposite wall portions which is remote from said ultrasonic probe, and
        a reflected wave recognition control portion configured to implement a reflected wave recognition control for each of a plurality of said reflected wave signals received by said ultrasonic probe at mutually different positions of reception in a longitudinal direction of said blood vessel, and for each of said front wall portion and said back wall portion, to detect according to a relationship between a magnitude of said each reflected wave signal and a position in a diametric direction of said blood vessel: (i) a first peak of said each reflected wave signal at which the magnitude is larger than a predetermined first peak determining threshold value; (ii) a bottom of said each reflected wave signal which is generated at a position of said blood vessel located outwardly of the position of generation of said first peak in the diametric direction of said blood vessel and at which the magnitude is smaller than a predetermined bottom determining threshold value; and (iii) a second peak of said each reflected wave signal which is generated at a position of said blood vessel located outwardly of the position of generation of said first peak in the diametric direction of said blood vessel but located within a spacing distance from the position of generation of the first peak less than a predetermined peak-to-peak distance threshold value, with said bottom being located therebetween, and at which the magnitude is larger than a predetermined second peak determining threshold value, and wherein said index value calculating portion calculates said front wall portion image clarity index value based on a number of the reflected wave signals all of said first peak, said bottom and said second peak of which have been detected by said reflected wave recognition control implemented by said reflected wave recognition control portion for said front wall portion, and said back wall portion image clarity index value on the based on a number of the reflected wave signals all of said first peak, said bottom and said second peak of which have been detected by said reflected wave recognition control implemented by said reflected wave recognition control portion for said back wall portion.

2. The ultrasonic blood vessel inspecting apparatus according to claim 1, wherein said reflected wave recognition control portion implements said reflected wave recognition control for those of said reflected wave signals which are received within a predetermined observation range in the longitudinal direction of said blood vessel.

3. The ultrasonic blood vessel inspecting apparatus according to claim 1, wherein said magnitude of said each reflected wave signal is an amplitude of said each reflected wave signal, or a brightness value obtained by conversion of said amplitude of said each reflected wave signal, which brightness value is used to display the longitudinal cross sectional image of said blood vessel on an image display.

4. The ultrasonic blood vessel inspecting apparatus according to claim 1, wherein said ultrasonic probe is provided with a pair of parallel ultrasonic detector arrays comprised of a first short-axis ultrasonic detector array and a second short-axis ultrasonic detector array each of which has a plurality of ultrasonic oscillators arranged linearly, and a long-axis ultrasonic detector array which is disposed adjacent to an intermediate portion of one or both of said first short-axis ultrasonic detector array and said second short-axis ultrasonic detector array and which has a plurality of ultrasonic oscillators arranged linearly, said first and second short-axis ultrasonic detector arrays and said long-axis ultrasonic detector array lying in one plane, and wherein said longitudinal cross sectional blood vessel image generating portion generates the longitudinal cross sectional image of said blood vessel, based on reflected wave signals of an ultrasonic wave received by said long-axis ultrasonic detector array in a state where the plurality of ultrasonic oscillators of each of said first short-axis ultrasonic detector array and said second short-axis ultrasonic detector array are arranged in a direction perpendicular to a longitudinal direction of said blood vessel and the plurality of ultrasonic oscillators of said long-axis ultrasonic detector array are arranged in the longitudinal direction of said blood vessel.

5. The ultrasonic blood vessel inspecting apparatus according to claim 4, wherein the executable portions further comprise:

an image display device having a first short-axis image display region for displaying an ultrasonic image obtained by said first short-axis ultrasonic detector array, a second short-axis image display region for displaying an ultrasonic image obtained by said second short-axis ultrasonic detector array, and a long-axis image display region for displaying the longitudinal cross sectional blood vessel image of said blood vessel;

a multi-axes drive device configured to position said ultrasonic probe;

a short-axis image position establishing portion configured to operate said multi-axes drive device to position said ultrasonic probe such that a distance between said first short-axis ultrasonic detector array and a center of said blood vessel is equal to a distance between said second short-axis ultrasonic detector array and the center of said blood vessel, and such that the image of said blood vessel is located at a widthwise central portion of each of said first short-axis image display region and said second short-axis image display region; and an ultrasonic probe position rectifying portion configured to operate said multi-axes drive device to position said ultrasonic probe after completion of positioning of said ultrasonic probe under the control of said short-axis image position establishing portion, such that a value calculated based on said front wall portion image clarity index value and said back wall portion image clarity index value is held within a predetermined target range.

6. The ultrasonic blood vessel inspecting apparatus according to claim 1, wherein the executable portions further comprise a blood vessel diameter measuring portion configured to measure in advance a rest-time diameter of said blood vessel before releasing of said blood vessel from blood flow obstruction, and a maximum diameter of said blood vessel after the releasing of said blood vessel from the blood flow obstruction, and calculates a maximum value of a diameter change ratio of said blood vessel after the releasing of said blood vessel from the blood flow obstruction, with respect to the rest-time diameter of said blood vessel, and wherein said index value calculating portion calculates a reliability index value indicative of a degree of reliability of the maximum value of the diameter change ratio of said blood vessel calculated by said blood vessel diameter measuring portion after the releasing of said blood vessel with respect to the rest-time diameter of said blood vessel, based on said front wall portion image clarity index value and said back wall portion image clarity index value at the time of measurement of said rest-time diameter, and said front wall portion image clarity index value and said back wall portion image clarity index value at the time of measurement of said maximum diameter.

7. The ultrasonic blood vessel inspecting apparatus according to claim 1, wherein said index value calculating portion commands an image display device to display said front wall portion image clarity index value and said back wall portion image clarity index value, as respective images which are continuously variable according to said index values and which are comparable with each other.

* * * * *